US012715934B2

(12) United States Patent
Sloan

(10) Patent No.: US 12,715,934 B2
(45) Date of Patent: Aug. 25, 2026

(54) ANTI-IDIOTYPE ANTIBODY MOLECULES AND USES THEREOF

(71) Applicant: Otsuka Pharmaceutical Co., Ltd., Osaka (JP)

(72) Inventor: Susan Sloan, Newton, MA (US)

(73) Assignee: Otsuka Pharmaceutical Co., Ltd., Osaka (JP)

( * ) Notice: Subject to any disclaimer, the term of this patent is extended or adjusted under 35 U.S.C. 154(b) by 771 days.

(21) Appl. No.: 18/165,408

(22) Filed: Feb. 7, 2023

(65) Prior Publication Data

US 2023/0383010 A1 Nov. 30, 2023

Related U.S. Application Data

(60) Provisional application No. 63/307,538, filed on Feb. 7, 2022.

(51) Int. Cl.
*C07K 16/42* (2006.01)
*C12N 15/63* (2006.01)
*G01N 33/577* (2006.01)

(52) U.S. Cl.
CPC .......... *C07K 16/4208* (2013.01); *C12N 15/63* (2013.01); *G01N 33/577* (2013.01); *C07K 2317/52* (2013.01); *C07K 2317/565* (2013.01)

(58) Field of Classification Search
CPC ............ C07K 16/4208; C07K 2317/52; C07K 2317/565; C07K 16/2875; C07K 2317/56; C12N 15/63; G01N 33/577; A61K 2039/505
See application file for complete search history.

(56) References Cited

U.S. PATENT DOCUMENTS 4,433,059 A 2/1984 Chang et al.
4,444,878 A 4/1984 Paulus
4,816,567 A 3/1989 Cabilly et al.
5,208,020 A 5/1993 Chari et al.
5,223,409 A 6/1993 Ladner et al.
5,225,539 A 7/1993 Winter
5,273,743 A 12/1993 Ahlem et al.
5,475,092 A 12/1995 Chari et al.
5,534,254 A 7/1996 Huston et al.
5,582,996 A 12/1996 Curtis
5,585,089 A 12/1996 Queen et al.
5,585,499 A 12/1996 Chari et al.
5,591,828 A 1/1997 Bosslet et al.
5,624,821 A 4/1997 Winter et al.
5,635,602 A 6/1997 Cantor et al.
5,637,481 A 6/1997 Ledbetter et al.
5,648,260 A 7/1997 Winter et al.
5,693,761 A 12/1997 Queen et al.
5,693,762 A 12/1997 Queen et al.
5,731,168 A 3/1998 Carter et al.
5,837,242 A 11/1998 Holliger et al.
5,837,821 A 11/1998 Wu
5,844,094 A 12/1998 Hudson et al.
5,846,545 A 12/1998 Chari et al.
5,864,019 A 1/1999 King et al.
5,869,620 A 2/1999 Whitlow et al.
5,910,573 A 6/1999 Plueckthun et al.
5,932,448 A 8/1999 Tso et al.
5,959,083 A 9/1999 Bosslet et al.
5,989,830 A 11/1999 Davis et al.
6,005,079 A 12/1999 Casterman et al.
6,239,259 B1 5/2001 Davis et al.
6,294,353 B1 9/2001 Pack et al.
6,333,396 B1 12/2001 Filpula et al.
6,476,198 B1 11/2002 Kang
6,511,663 B1 1/2003 King et al.
6,670,453 B2 12/2003 Frenken et al.
6,743,896 B2 6/2004 Filpula et al.
6,809,185 B1 10/2004 Schoonjans et al.
6,833,441 B2 12/2004 Wang et al.
7,129,330 B1 10/2006 Little et al.
7,183,076 B2 2/2007 Arathoon et al.
7,189,820 B2 3/2007 Ruben
7,521,056 B2 4/2009 Chang et al.
7,527,787 B2 5/2009 Chang et al.
7,534,866 B2 5/2009 Chang et al.
7,612,181 B2 11/2009 Wu et al.
8,105,603 B2 1/2012 Kelley et al.
8,895,705 B2 11/2014 Medema et al.
9,000,128 B2 4/2015 Medema et al.
9,969,808 B2 5/2018 van Eenennaam et al.
10,107,821 B2 10/2018 Van Eenennaam et al.
10,377,830 B2 8/2019 van Eenennaam et al.
(Continued)

FOREIGN PATENT DOCUMENTS

EP 0173494 A2 3/1986
EP 0184187 A2 6/1986
(Continued)

OTHER PUBLICATIONS

Almagro et al., Front. Immunol. 2018; 8:1751 (Year: 2018).*
Chiu ML et al. Antibodies 2019 8, 55, 1-80 (Year: 2019).*
De Nardis, Camilla, et al. "A new approach for generating bispecific antibodies based on a common light chain format and the stable architecture of human immunoglobulin G1." Journal of Biological Chemistry 292.35 (2017): 14706-14717 (Year: 2017).*
Janeway, Immunobiology The Immune System in Health and Disease, 5th edition, 2001, Chapter 7 (Year: 2001).*
Wijesuriya et al. Protein Expression and Purification, 2018, 149:75-83 (Year: 2018).*
Altschul, S. F., et al., "Gapped BLAST and PSI-BLAST: A New Generation of Protein Database Search Programs," Nucleic Acids Research 25(17):3389-3402, Oxford University Press, United Kingdom (Sep. 1997).
Altschul, S.F., et al., "Basic Local Alignment Search Tool," Journal of Molecular Biology 215(3):403-410, Elsevier, Netherlands (Oct. 1990).
(Continued)

*Primary Examiner* — Gregory S Emch
*Assistant Examiner* — Kathleen Cunningchen
(74) *Attorney, Agent, or Firm* — Sterne, Kessler, Goldstein & Fox P.L.L.C.

(57) ABSTRACT

Antibody molecules that specifically bind to anti-APRIL antibody are disclosed. The antibody molecules can be used in assays for detecting anti-APRIL antibodies.

23 Claims, 11 Drawing Sheets

Specification includes a Sequence Listing.

(56) References Cited

U.S. PATENT DOCUMENTS 10,385,123 B2 8/2019 Myette et al.
10,954,296 B2 3/2021 Myette et al.
10,968,270 B2 4/2021 Myette et al.
10,981,982 B2 4/2021 Myette et al.
11,136,385 B2 10/2021 Myette et al.
2002/0004587 A1 1/2002 Miller et al.
2002/0076406 A1 6/2002 Leung
2002/0081296 A1 6/2002 Theill et al.
2002/0103345 A1 8/2002 Zhu
2003/0059862 A1 3/2003 Ruben
2003/0082175 A1 5/2003 Schneider et al.
2003/0207346 A1 11/2003 Arathoon et al.
2003/0211078 A1 11/2003 Heavner
2004/0219643 A1 11/2004 Winter et al.
2004/0220388 A1 11/2004 Mertens et al.
2004/0242847 A1 12/2004 Fukushima et al.
2005/0003403 A1 1/2005 Rossi et al.
2005/0004352 A1 1/2005 Kontermann et al.
2005/0069552 A1 3/2005 Bleck et al.
2005/0079170 A1 4/2005 Le Gall et al.
2005/0100543 A1 5/2005 Hansen et al.
2005/0136049 A1 6/2005 Ledbetter et al.
2005/0136051 A1 6/2005 Scallon
2005/0163782 A1 7/2005 Glaser et al.
2005/0266425 A1 12/2005 Zauderer et al.
2006/0073146 A1 4/2006 Ashkenazi et al.
2006/0083747 A1 4/2006 Winter et al.
2006/0120960 A1 6/2006 Deyev et al.
2006/0204493 A1 9/2006 Huang et al.
2006/0263367 A1 11/2006 Fey et al.
2007/0004909 A1 1/2007 Johnson et al.
2007/0087381 A1 4/2007 Kojima
2007/0128150 A1 6/2007 Norman
2007/0141049 A1 6/2007 Bredehorst et al.
2007/0154901 A1 7/2007 Thogersen et al.
2007/0160603 A1 7/2007 Ruben
2007/0274985 A1 11/2007 Dubel et al.
2008/0050370 A1 2/2008 Glaser et al.
2008/0069820 A1 3/2008 Fuh et al.
2008/0152645 A1 6/2008 Pardridge et al.
2008/0171855 A1 7/2008 Rossi et al.
2008/0241884 A1 10/2008 Shitara et al.
2008/0254512 A1 10/2008 Capon
2008/0260737 A1 10/2008 Ponce et al.
2008/0260738 A1 10/2008 Moore et al.
2009/0130106 A1 5/2009 Christopherson et al.
2009/0148905 A1 6/2009 Ashman et al.
2009/0155275 A1 6/2009 Wu et al.
2009/0162359 A1 6/2009 Klein et al.
2009/0162360 A1 6/2009 Klein et al.
2009/0175851 A1 7/2009 Klein et al.
2009/0175867 A1 7/2009 Thompson et al.
2009/0232811 A1 9/2009 Klein et al.
2009/0234105 A1 9/2009 Gervay-Hague et al.
2009/0263392 A1 10/2009 Igawa et al.
2009/0274649 A1 11/2009 Qu et al.
2012/0195909 A1 8/2012 Medema et al.
2012/0201823 A1 8/2012 Janatpour et al.
2013/0156769 A1 6/2013 Kufer et al.
2013/0273064 A1 10/2013 Medema et al.
2013/0295103 A1 11/2013 Medema et al.
2013/0302353 A1 11/2013 Medema et al.
2014/0161828 A1 6/2014 Armitage et al.
2016/0202267 A1 7/2016 Van Eenennaam et al.
2016/0264674 A1 9/2016 van Eenennaam et al.
2017/0145086 A1 5/2017 Myette et al.
2017/0369582 A1 12/2017 Huard et al.
2018/0258176 A1 9/2018 van Eenennaam et al.
2019/0092851 A1 3/2019 Myette et al.
2019/0330326 A1 10/2019 Myette et al.
2020/0079859 A1 3/2020 van Eenennaam et al.
2020/0299376 A1 9/2020 Myette et al.
2020/0317770 A1 10/2020 Myette et al.
2020/0331995 A1 10/2020 Myette et al.
2021/0032324 A1 2/2021 Myette et al.
2021/0340266 A1 11/2021 Myette et al.
2022/0235124 A1 7/2022 Myette et al.

FOREIGN PATENT DOCUMENTS

EP 0346087 A2 12/1989
EP 0388151 A1 9/1990
EP 0171496 B1 5/1993
EP 0125023 B2 3/2002
EP 0519596 B1 2/2005
EP 1255558 B1 6/2006
EP 1666052 B1 6/2011
EP 2403528 B1 4/2016
EP 3103476 A2 12/2016
GB 2188638 A 10/1987
JP 2004537290 A 12/2004
JP 2011500073 A 1/2011
JP 2011501945 A 1/2011
JP 2011502126 A 1/2011
JP 2011523037 A 8/2011
JP 2012519198 A 8/2012
JP 5062606 B2 10/2012
JP 2013512258 A 4/2013
JP 2013541522 A 11/2013
JP 2014523408 A 9/2014
NO 2016113368 A1 7/2016
RU 2013151455 A 5/2015
WO WO-8601533 A1 3/1986
WO WO-8702671 A1 5/1987
WO WO-9002809 A1 3/1990
WO WO-9100906 A1 1/1991
WO WO-9103493 A1 3/1991
WO WO-9110741 A1 7/1991
WO WO-9117271 A1 11/1991
WO WO-9201047 A1 1/1992
WO WO-9203917 A1 3/1992
WO WO-9203918 A1 3/1992
WO WO-9209690 A2 6/1992
WO WO-9215679 A1 9/1992
WO WO-9218619 A1 10/1992
WO WO-9220791 A1 11/1992
WO WO-9301288 A1 1/1993
WO WO-9323537 A1 11/1993
WO WO-9404678 A1 3/1994
WO WO-9409131 A1 4/1994
WO WO-9412625 A2 6/1994
WO WO-9509917 A1 4/1995
WO WO-9637621 A2 11/1996
WO 1999012965 A2 3/1999
WO 1999012965 A3 6/1999
WO WO-9964460 A1 12/1999
WO WO-0006605 A2 2/2000
WO 200160397 A1 8/2001
WO WO-02072635 A2 9/2002
WO 2002094192 A2 11/2002
WO WO-2004081051 A1 9/2004
WO 2005075511 A1 8/2005
WO WO-2006020258 A2 2/2006
WO WO-2006106905 A1 10/2006
WO 2007039489 A1 4/2007
WO WO-2007044887 A2 4/2007
WO WO-2007095338 A2 8/2007
WO WO-2007110205 A2 10/2007
WO WO-2007137760 A2 12/2007
WO WO-2008119353 A1 10/2008
WO WO-2009021754 A2 2/2009
WO WO-2009068630 A1 6/2009
WO WO-2009089004 A1 7/2009
WO 2010100056 A2 9/2010
WO 2010100056 A3 11/2010
WO WO-2010129304 A2 11/2010
WO 2011047121 A1 4/2011
WO WO-2011131746 A2 10/2011
WO 2012163805 A1 12/2012
WO WO-2013060867 A2 5/2013
WO 2014151680 A1 9/2014
WO 2015034364 A1 3/2015
WO 2015069865 A1 5/2015

(56) References Cited

FOREIGN PATENT DOCUMENTS

| | | | |
|---|---|---|---|
| WO | WO-2015095766 A2 * | 6/2015 | ......... A61K 47/6851 |
| WO | 2016110587 A1 | 7/2016 | |
| WO | 2017091683 A1 | 6/2017 | |
| WO | WO-2017093942 A1 * | 6/2017 | .............. A61P 43/00 |
| WO | 2020144535 A1 | 7/2020 | |
| WO | 2021262999 A1 | 12/2021 | |
| WO | 2023150778 A1 | 8/2023 | |

OTHER PUBLICATIONS

Barbas, C.F., et al., "Assembly of Combinatorial Antibody Libraries on Phage Surfaces: The Gene III Site," Proceedings of the National Academy of Sciences of the United States of America 88(18):7978-7982, National Academy of Sciences, United States (Sep. 1991).

Beidler, C.J., et al., "Cloning and High Level Expression of a Chimeric Antibody With Specificity for Human Carcinoembryonic Antigen," Journal of Immunology 141(11):4053-4060, American Association of Immunologists, United States (1988).

Better, M., et al., "Escherichia Coli Secretion of an Active Chimeric Antibody Fragment," Science 240(4855):1041-1043, Association for the Advancement of Science, United States (May 1988).

Bird, R.E., et al., "Single-chain Antigen-binding Proteins," Science 242(4877):423-426, Association for the Advancement of Science, United States (Oct. 1988).

Brown, N.P., et al., "Mview: a Web-compatible Database Search or Multiple Alignment Viewer," Bioinformatics 14(4):380-381, Oxford University Press, United Kingdom (1998).

Brúggemann, M., et al., "Human antibody production in transgenic mice: expression from 100 kb of the human IgH locus," Eur J Immunol, 21(5): 1323-1326, Wiley, United States (May 1991).

Brúggemann, M., et al., "Designer Mice: The Production of Human Antibody Repertoires in Transgenic Animals," The Year in Immunology 7:33-40, Karger, Switzerland (1993).

Castigli, E., et al., "Impaired IgA class switching in APRIL-deficient mice," Proceedings of the National Academy of Sciences of the United States of America 101(11):3903-3908, National Academy of Sciences, United States (Mar. 2004).

Chothia, C., and Lesk, A.M., "Canonical Structures for the Hypervariable Regions of Immunoglobulins," Journal of Molecular Biology 196(4):901-917, Elsevier, Netherlands (Aug. 1987).

Clackson, T., et al., "Making Antibody Fragments using Phage Display Libraries," Nature 352(6336):624-628, Nature Publishing Group, United Kingdom (Aug. 1991).

Colcher, D., et al., "Single-chain Antibodies in Pancreatic Cancer," Annals of the New York Academy of Sciences 880:263-280, Blackwell, United States (Jun. 1999).

Edgar, R.C., "Muscle: a Multiple Sequence Alignment Method With Reduced Time and Space Complexity," Biomed Central Bioinformatics 5:113, BioMed Central, United Kingdom (Aug. 2004).

Edgar, R.C., "Muscle: Multiple Sequence Alignment With High Accuracy and High Throughput," Nucleic Acids Research 32(5):1792-1797, Oxford University Press, United Kingdom (Mar. 2004).

Emancipator, S.N., et al., "Animal Models of IgA Nephropathy," Current Protocols in Immunology. Chapter 15(Suppl 29):Unit 15.11. 1-15.11.18, Wiley, United States (May 2001).

Endo, Y., "Iga Nephropathy—human Disease and Animal Model," Renal Failure 19(3):347-371, Informa Healthcare, United Kingdom (May 1997).

Fuchs, P., et al., "Targeting Recombinant Antibodies to the Surface of *Escherichia coli*: Fusion to a Peptidoglycan Associated Lipoprotein," Nature Biotechnology 9:1369-1372, Springer Nature, Germany (Dec. 1991).

Garrard, L.J., et al., "Fab Assembly and Enrichment in a Monovalent Phage Display System," Biotechnology 9(12):1373-1377, Nature Publishing Group, United States (Dec. 1991).

Gerhard, D.S., et al., "The Status, Quality, and Expansion of the Nih Full-length Cdna Project: the Mammalian Gene Collection (Mgc)," Genome Research 14(10B):2121-2127, Cold Spring Harbor Laboratory Press, United States (Oct. 2004).

Gram, H., et al., "In Vitro Selection and Affinity Maturation of Antibodies From a Naive Combinatorial Immunoglobulin Library," Proceedings of the National Academy of Sciences of the United States of America 89(8):3576-3580, National Academy of Sciences, United States (Apr. 1992).

Green, L.L., et al., "Antigen-specific Human Monoclonal Antibodies from Mice Engineered with Human Ig Heavy and Light Chain YACs," Nature Genetics 7(1):13-21, Nature Publishing Company, United States (May 1994).

Griffiths, A.D., et al., "Human Anti-Self Antibodies with High Specificity from Phage Display Libraries," The EMBO Journal 12(2):725-734, Wiley Blackwell, United Kingdom (Feb. 1993).

Hawkins, R.E., et al., "Selection of phage antibodies by binding affinity. Mimicking affinity maturation," Journal of Molecular Biology 226(3):889-896, Elsevier Science, United States (Aug. 1992).

Hay, B.N., et al., "Bacteriophage Cloning and *Escherichia coli* Expression of a Human IgM Fab," Human Antibodies and Hybridomas 3(2):81-85, Butterworth-Heinemann, United States (Apr. 1992).

Hoogenboom, H.R., et al., "Multi-subunit Proteins on the Surface of Filamentous Phage: Methodologies for Displaying Antibody (Fab) Heavy and Light Chains," Nucleic Acids Research 19(15):4133-4137, Oxford University Press, United Kingdom (Aug. 1991).

Huse, W.D., et al., "Generation of a Large Combinatorial Library of the Immunoglobulin Repertoire in Phage Lambda," Science 246(4935):1275-1281, American Association for the Advancement of Science, United States (Dec. 1989).

Huston, U.S., et al., "Protein Engineering of Antibody Binding Sites: Recovery of Specific Activity in an Anti-digoxin Single-chain Fv Analogue Produced in *Escherichia coli*," Proc Natl Acad Sci USA 85(16):5879-5883, National Academy of Sciences, United States (Aug. 1988).

Imai, H., et al., "Spontaneous Glomerular Iga Deposition in Ddy Mice: an Animal Model of Iga Nephritis," Kidney International 27(5):756-761, Elsevier, United States (May 1985).

Jones, P.T., et al., "Replacing the Complementarity-determining Regions in a Human Antibody with those from a Mouse," Nature 321(6069):522-525, Nature Publishing Group, United Kingdom (May 1986).

Kabat, E.A., et al., "Sequences of Proteins of Immunological Interest," 5th Edition, NIH publication No. 91-3242 : 1-1137, U.S. Department of Public Health and Human Services, National Institutes of Health, United States (1991).

Kakani, S., et al., "The Gne M712t Mouse as a Model for Human Glomerulopathy," The American Journal of Pathology 180(4):1431-1440, Elsevier, United States (Apr. 2012).

Katoh, K. and Standley, D.M., "Mafft Multiple Sequence Alignment Software Version 7: Improvements in Performance and Usability," Molecular Biology and Evolution 30(4):772-780, Oxford University Press, United States (Apr. 2013).

Kelly, K., et al., "April/trdl-1, a Tumor Necrosis Factor-like Ligand, Stimulates Cell Death," Cancer Research 60(4):1021-1027, Baltimore, United States (Feb. 2000).

Lassmann, T., et al., "Kalign—an Accurate and Fast Multiple Sequence Alignment Algorithm," Biomed Central Bioinformatics 6:298, BioMed Central, Unted Kingdom (Dec. 2005).

Lassmann, T., et al., "Kalign2: High-performance Multiple Alignment of Protein and Nucleotide Sequences Allowing External Features," Nucleic Acids Research 37(3):858-865, Oxford University Press, United Kingdom (Feb. 2009).

Li, W. et al., "The EMBL-EBI Bioinformatics Web and Programmatic Tools Framework," Nucleic Acids Research 43(W1):W580-W584, Oxford University Press, United Kingdom (Jul. 2015).

Liu, A.Y., et al., "Production of a Mouse-Human Chimeric Monoclonal Antibody to CD20 with Potent Fc-Dependent Biologic Activity," Journal of Immunology 139(10):3521-3526, American Association of Immunologists, United States (Nov. 1987).

Liu, A.Y., et al., "Chimeric Mouse-human IgG1 Antibody that can Mediate Lysis of Cancer Cells," Proceedings of the National Academy of Sciences 84:3439-3443, National Academy of Sciences, United States (May 1987).

Lobuglio, A.F., et al., "Phase I Clinical Trial of Co17-la Monoclonal Antibody," Hybridoma 5(Suppl 1):S117-S123, Mary Ann Liebert, United States (Jul. 1986).

(56) References Cited

OTHER PUBLICATIONS

Lonberg, N., et al., "Antigen-specific Human Antibodies from Mice Comprising Four Distinct Genetic Modifications," Nature 368(6474):856-859, Nature Publishing Group, United States (Apr. 1994).
Martin, A. C. R., "Chapter 31: Protein Sequence and Structure Analysis of Antibody Variable Domains" in *Antibody Engineering,* Kontermann and Dubel, eds., pp. 422-439, Springer-Verlag, Germany (2001).
McWilliam, H., et al., "Analysis Tool Web Services from the EMBL-EBI," Nucleic Acids Research 41:W597-W600, Oxford University Press, United Kingdom (May 2013).
Montinaro, V., et al., "Evolution of Renal Injury in a Chronic Model of Iga Immune-complex-associated Nephropathy," Nephrol Dial Transplant 10(11):2035-2042, Oxford University Press, United Kingdom (Nov. 1995).
Morrison, S.L., et al., "Chimeric Human Antibody Molecules: Mouse Antigen-binding Domains with Human Constant Region Domains," Proceedings of the National Academy of Sciences USA 81(21):6851-6855, National Academy of Sciences, United States (Nov. 1984).
Morrison, S.L., "Transfectomas Provide Novel Chimeric Antibodies," Science 229(4719):1202-1207, Association for the Advancement of Science, United States (Sep. 1985).
Myers, E.W., et al., "Optimal Alignments in Linear Space," Computer Applications in the Biosciences 4(1):11-17, Oxford University Press, United Kingdom (Mar. 1988).
Needleman, S.B. and Wunsch, C.D., "A General Method Applicable to the Search for Similarities in the Amino Acid Sequence of Two Proteins," Journal of Molecular Biology 48(3):443-453, Elsevier, Netherlands (Mar. 1970).
Nishimura. Y., et al., "Recombinant Human-mouse Chimeric Monoclonal Antibody Specific for Common Acute Lymphocytic Leukemia Antigen," Cancer Research 47(4):999-1005, American Association for Cancer Research, United States (Feb. 1987).
Oi, V.T., and Morrison, S.L., "Chimeric Antibodies," BioTechniques, The Journal of Laboratory Technology for Bio-research 4(3):214-221, Eaton, United States (May-Jun. 1986).
Ota, T., et al., "Complete Sequencing and Characterization of 21,243 Full-length Human Cdnas," Nature Genetics 36(1):40-45, Nature Pub, United States (Jan. 2004).
Pradet-Balade, B., et al., "An Endogenous Hybrid Mrna Encodes Twe-pril, a Functional Cell Surface Tweak-april Fusion Protein," The Embo Journal 21(21):5711-5720, Nature Publishing Group, United Kingdom (Nov. 2002).
Reiter, Y., and Pastan, I., "Antibody Engineering of Recombinant Fv Immunotoxins for Improved Targeting of Cancer: Disulfide-stabilized Fv Immunotoxins," Clinical Cancer Research 2(2):245-252, Denville, United States (Feb. 1996).
Rifai, A., et al., "Experimental Iga Nephropathy," The Journal of Experimental Medicine 150(5):1161-1173, Rockefeller University Press, United States (Nov. 1979).
Rifai, A., "Experimental Models for Iga-associated Nephritis," Kidney International 31(1):1-7, Elsevier, United States (Jan. 1987).
Robinson, J.R., ed., *Sustained and Controlled Release Drug Delivery Systems,* Marcel Dekker, Inc., New York, United States (1978).
Saleh, M.N., et al., "A Phase Ii Trial of Murine Monoclonal Antibody 17-la and Interferon-gamma: Clinical and Immunological Data," Cancer Immunology and Immunotherapy 32(3):185-190, Springer Verlag, Germany (May 1990).
Shaw, D.R., et al., "Mouse/human Chimeric Antibodies to a Tumor-associated Antigen: Biologic Activity of the Four Human IgG Subclasses," Journal of the National Cancer Institute 80(19):1553-1559, Oxford University Press, United States (Dec. 1988).
Shu, H.B., et al., "Tall-1 is A Novel Member of the TNF Family that is Down-Regulated by Mitogens," Journal of Leukocyte Biology 65(5):680-683, Society for Leukocyte Biology, United States (May 1999).
Sievers, F., et al., "Fast, Scalable Generation of High-quality Protein Multiple Sequence Alignments Using Clustal Omega," Molecular Systems Biology 7:539, Wiley Blackwell, United Kingdom (Oct. 2011).
Sun, L.K., et al., "Chimeric Antibody With Human Constant Regions and Mouse Variable Regions Directed Against Carcinoma-associated Antigen 17-1A," Proceedings of the National Academy of Sciences of the United States of America 84(1):214-218, National Academy of Sciences, United States (Jan. 1987).
Tomino, Y., "IgA Nephropathy: Lessons From an Animal Model, the ddY Mouse," Journal of Nephrology 21(4):463-467, Springer, Italy (Jul. 2008).
Tuaillon, N., et al., "Human Immunoglobulin Heavy-chain Minilocus Recombination in Transgenic Mice: Gene-segment Use in Mu and Gamma Transcripts," Proceedings of the National Academy of Sciences of the United States of America 90(8):3720-3724, National Academy of Sciences, United States (Apr. 1993).
Verhoeyen, M., et al., "Reshaping Human Antibodies: Grafting an Antilysozyme Activity," Science 239(4847):1534-1536, Washington, United States (Mar. 1988).
Wood, C.R., et al., "The Synthesis and in Vivo Assembly of Functional Antibodies in Yeast," Nature 314(6010):446-449, Nature Publishing Group, England (Apr. 1985).
Zhang, L., et al., "Establishment of a Mouse Iga Nephropathy Model With the Mbp-20-peptide Fusion Protein," Anatomical Record 293(10): 1729-1737, Hoboken, United States (Oct. 2010).
[No Author Listed] Purified anti-mouse CD256 (April) Antibody-BioLegend, Version 5 Revised (2015) retrieved from biolegend.com/en-us/products/purified-anti-mouse-cd256-april-antibody-6360.
Anonymous "(MAB5860) Human APRIL/TNFSF13 Antibody—R&D Systems—CiteAb" (2014) Retrieved from the Internet Feb. 1, 2017, www.citeab.com/antibodies/699338-mab5860-human-april-tnfsf13-antibody.
Anonymous: "Visionary Study: Phase 3 Trial of Sibeprenlimab in Immunoglobulin A Nephropathy (IgAN)."ClinicalTrials.gov (2022): 1-7, Retrieved from the Internet: <URL:https://classic.clinicaltrials.gov/ct2/show/NCT05248646> [retrieved on Jun. 29, 2023].
Anonymous: "Visionary Study: Phase 3 Trial of Sibeprenlimab in View this study on the modernized ClinicalTrials. gov Study Details Tabular View No. Results Posted Disclaimer How to Read a Study Record Visionary Study: Phase 3 Trial of Sibeprenlimab in Immunoglobulin A Nephropathy ( IgAN). "(2022): 1-8, Retrieved from the Internet: < URL: https://classic.clinicaltrials.gov/ct2/show/NCT05248646> [retrieved on Jun. 29, 2023].
Colman, P.M. "Effects of amino acid sequence changes on antibody-antigen interactions," Research in Immunology, Elsevier, NY, 145(1):33-36, 1994.
Du, B. et al., "Preparation of Polyclonal Antibody Against sAPRIL and Analysis of Function in Suppressing sAPRIL- Mediated Lymphocyte Proliferation", Chinese Journal of Experimental Hematology, vol. 19, No. 4, pp. 1019-1022 (2011) [English Abstract].
Dulos, J. et al. "Development of a first in class APRIL fully blocking antibody BION-1301 for the treatment of multiple myeloma," Abstract from the American Association for Cancer Research Annual Meeting, Apr. 1-5, 2017, 2 pages.
Gao, Q. et al., "In Vitro and In Vivo Evaluation of a Humanized Anti-APRIL Antibody," Current Molecular Medicine (2013) vol. 13, pp. 464-465.
Guadagnoli, M. et al., "Development and characterization of APRIL antagonistic monoclonal antibodies for treatment of B-cell lymphomas," Blood (2011) vol. 117, No. 25, pp. 6856-6865.
Jahne, M. et al. "APRIL, a New Ligand of the Tumor Necrosis Factor Family, Stimulates Tumor Cell Growth," J Exp Med (1998) vol. 188, No. 6, pp. 1185-1190.
Hart, M. H. et al. "Differential effect of drug interference in immunology assays," Journal of Immunological Methods vol. 372 (2011): 196-203.
Huard, B. et al., "Selective APRIL Blockade Delays Systemic Lupus Erythematosus in Mouse," PLOS ONE (2012) vol. 7, No. 2, e31837.
International Search Report and Written Opinion in International Patent Application No. PCT/US2016/063518 dated Mar. 1, 2017.

(56) References Cited

OTHER PUBLICATIONS

International Search Report and Written Opinion in International Patent Application No. PCT/US2021/038924 dated Oct. 29, 2021.
International Search Report and Written Opinion in International Patent Application No. PCT/US2023/062098 dated May 16, 2023.
Kim, Y.G. et al., "Pathogenic Role of a Proliferation-Inducing Ligand (APRIL) in Murine IgA Nephropathy," PLOS One (2015) vol. 10, No. 9, Article e0137044, 13 pages.
Lin, L. et al. "A First in Class APRIL Fully Blocking Antibody Targets Novel Immune Regulation of APRIL in Multiple Myeloma: Further Therapeutic Implication," Blood (2017) vol. 130, p. 499. Abstract Only.
Mariuzza et al., "The Structural Basis of Antigen-Antibody Recognition," Ann Rev Biophys Biophys Chem (1987) vol. 16, pp. 139-159.
McConnell, A.D. et al., "An integrated approach to extreme thermostabilization and affinity maturation of an antibody," Protein Engineering, Design & Selection (2013) vol. 26, No. 2, 13 pages.
Myette, J.R. et al., "A Proliferation Inducing Ligand (APRIL) targeted antibody is a safe and effective treatment of murine IgA nephropathy," Kidney International (2019) 16 pages.
Novak, J. et al., "Aberrant Glycosylation of the IgA1 Molecule in IgA Nephropathy," Seminars in Nephrology (2018), vol. 38, No. 5, pp. 461-476.
Osório, C. et al., "Selective regulation of axonal growth from developing hippocampal neurons by tumor necrosis factor superfamily member APRIL," Molecular and Cellular Neuroscience (2014) vol. 59, pp. 24-36.
Paul, W.E. Fundamental Immunology, 3rd ed. Raven Press, NY, Chap. 9, pp. 292-295, 1993.
Rudikoff, S. et al. "Single Amino Acid Substitution Altering Antigen-Binding Specificity." Proc. Natl. Acad. Sci. USA (1982) 79:1979-1983.
Ryan, M.C. et al., "Targeting of BAFF and APRIL for autoimmunity and oncology," Adv Exp Med Biol (2009) vol. 647, pp. 52-63.
Safdari, Y. et al., "Antibody humanization methods—a review and update," Biotechnology and Genetic Engineering Reviews (2013) vol. 29, No. 2, pp. 175-186.
Selvaskandan, H. et al. "New strategies and perspectives on managing IgA nephropathy," Clinical and Experimental Nephrology (2019) vol. 23, pp. 577-588.
Suzuki, Y. et al. "MO258 Safety, tolerability, pharmacokinetics and pharmacodynamics of VIS649, an APRIL-neutralizing IgG2 monoclonal antibody, in healthy volunteers: Phase 1, randomized, double-blind, placebo-controlled, single ascending dose study." Nephrology Dialysis Transplantation vol. 36 No. Supplement_1 (2021).
Vajdos, F.F. et al., "Comprehensive Functional Maps of the Antigen-Binding Site of an anti-ErbB2 Antibody Obtained With Shotgun Scanning Mutagenesis," J Mol Biol (2002) vol. 320, No. 2, pp. 415-428.
Wollacott, A.M. et al., "Structural prediction of antibody-APRIL complexes by computational docking constrained by antigen saturation mutagenesis library data," J Mol Recognition (2019) Article e2778, 12 pages.
Yamasaki, K. et al., "Galactose-Deficient IgA1-Specific Antibody Recognizes GalNAc-Modified Unique Epitope on Hinge Region of IgA1," Monoclonal Antibodies in Immunodiagnosis and Immunotherapy vol. 37, No. 6. (2018) pp. 252-256.

* cited by examiner

ANTI-IDIOTYPE ANTIBODY MOLECULES AND USES THEREOF

CROSS-REFERENCE TO RELATED APPLICATIONS

This application claims the benefit of U.S. Provisional Application No. 63/307,538, filed Feb. 7, 2022. The contents of the aforementioned application are hereby incorporated by reference in their entirety.

SEQUENCE LISTING

The instant application contains a Sequence Listing which has been submitted electronically in XML format and is hereby incorporated by reference in its entirety. Said XML copy, created on Mar. 31, 2023, is named P2029-703510_SL.xml and is 24,334 bytes in size.

BACKGROUND

IgA nephropathy is one of the most prevalent, chronic glomerular diseases worldwide. Conservative epidemiological estimates cite a global incidence of approximately 5-50 cases/million (children) and 10-40 cases/million (adults). This incidence of disease presents a regional bias with a higher prevalence in Asia and the Americas, with a particularly higher disease burden in Japan and regions of China. Biopsy confirmed cases of IgA nephropathy in Japan are projected at approximately 350,000. In the US, this projection is approximately 100,000—as such, it is the most frequently diagnosed 1° glomerular disease in adults. While a relatively indolent disease, IgA nephropathy leads to end stage renal disease (ESRD), i.e., renal failure in 20-50% of patients within a 20-30 year span. These numbers are likely grossly underreported given the need to confirm the disease by kidney biopsy, a protocol that is variably practiced in various clinical settings. The disease has a complex pathogenesis with genetic, epidemiological, and potentially environmental components to disease etiology, pathology, and progression. It likewise has a variable clinical presentation ranging from asymptomatic to end-stage renal failure (ESRD). IgA nephropathy is caused by the deposition of IgA, typically in the form of immune complexes in the mesangium of the kidney.

Antibody drug products are being developed for the treatment of IgA nephropathy. There is a need for developing new agents and assays for the evaluation of antibody drug products in preclinical and clinical samples.

SUMMARY

This disclosure provides, at least in part, antibody molecules that bind to an anti-APRIL antibody, e.g., sibeprenlimab, and that comprise one or more functional and structural properties disclosed herein. In an embodiment, the antibody molecule is an anti-idiotype (anti-ID) antibody molecule. In an embodiment, the antibody molecule binds to and/or reduces (e.g., inhibits, blocks, or neutralizes) one or more biological activities of the anti-APRIL antibody. In an embodiment, the antibody molecule comprises a heavy chain variable region (VH) and/or a light chain variable region (VL), as described herein. In an embodiment, the antibody molecule comprises one or more heavy chain CDRs (HCDRs) of an VH and/or one or more light chain CDRs (LCDRs) of an VL, as described herein. Nucleic acid molecules encoding the antibody molecules, vectors, cells, compositions, kits, and methods for making and using the antibody molecules, are also provided. The antibody molecules disclosed herein are suitable for use in the detection and measurement of anti-APRIL antibodies (e.g., sibeprenlimab) in samples and subjects.

Accordingly, in an aspect, this disclosure provides an antibody molecule (e.g., an anti-idiotype antibody molecule), e.g., an antibody molecule described herein, having one or more (e.g., 1, 2, 3, 4, 5, 6, 7, 8, 9, 10, 11, 12, or all) of the following properties:

a) Binds to an anti-APRIL antibody (e.g., sibeprenlimab) with high affinity, e.g., with a half maximal effective concentration ($EC_{50}$) of about 1 μg/mL or less, e.g., about 900 ng/ml or less, 800 ng/ml or less, 700 ng/ml or less, 600 ng/ml or less, 500 ng/ml or less, 400 ng/ml or less, 300 ng/ml or less, 200 ng/ml or less, 100 ng/ml or less, 90 ng/ml or less, 80 ng/ml or less, 70 ng/ml or less, 60 ng/ml or less, 50 ng/ml or less, 40 ng/mL or less, 30 ng/ml or less, 20 ng/ml or less, 10 ng/ml or less, 5 ng/ml or less, 2 ng/ml or less, 1 ng/ml or less, e.g., between 1 ng/mL and 1 μg/mL, e.g., between 1 ng/ml and 1 μg/mL, between 1 ng/ml and 500 ng/mL, between 1 ng/mL and 200 ng/mL, between 1 ng/ml and 100 ng/ml, between 1 ng/mL and 50 ng/mL, between 1 ng/mL and 20 ng/mL, between 1 ng/ml and 10 ng/mL, between 1 ng/mL and 5 ng/mL, between 2 ng/ml and 1 μg/mL, between 5 ng/ml and 1 μg/mL, between 10 ng/mL and 1 μg/mL, between 20 ng/mL and 1 μg/mL, between 50 ng/ml and 1 μg/mL, between 100 ng/ml and 1 μg/mL, between 200 ng/ml and 1 μg/mL, between 500 ng/mL and 1 μg/mL, between 2 ng/mL and 500 ng/mL, between 5 ng/ml and 200 ng/mL, between 10 ng/mL and 100 ng/mL, between 15 ng/mL and 50 ng/mL, between 20 ng/ml and 30 ng/ml, between 20 ng/ml and 25 ng/ml, e.g., about 1 ng/mL, 2 ng/ml, 5 ng/mL, 10 ng/mL, 15 ng/mL, 20 ng/mL, 25 ng/mL, 30 ng/mL, 40 ng/mL, 50 ng/mL, 60 ng/mL, 70 ng/mL, 80 ng/mL, 90 ng/mL, 100 ng/mL, 110 ng/mL, 120 ng/mL, 130 ng/ml, 140 ng/mL, or 150 ng/ml, e.g., as determined by a method described herein;

b) Binds specifically to an idiotype on an anti-APRIL antibody (e.g., sibeprenlimab), e.g., the same, similar, or overlapping epitope as the epitope recognized by a monoclonal antibody described herein (e.g., mAb 1H4);

c) Reduces (e.g., inhibits, blocks, or neutralizes) one or more biological activities of an anti-APRIL antibody (e.g., sibeprenlimab), in vitro, ex vivo, or in vivo;

d) Shows the same or similar binding affinity or specificity, or both, as a monoclonal antibody described herein (e.g., mAb 1H4);

e) Shows the same or similar binding affinity or specificity, or both, as an antibody molecule comprising a heavy chain variable region and/or light chain variable region described herein, e.g., a heavy chain variable region and/or light chain variable region of a monoclonal antibody described herein (e.g., mAb 1H4);

f) Shows the same or similar binding affinity or specificity, or both, as an antibody molecule comprising one or more (e.g., two or three) heavy chain CDRs and/or one or more (e.g., two or three) light chain CDRs described herein, e.g., one or more (e.g., two or three) heavy chain CDRs and/or one or more (two or three) light chain CDRs of a monoclonal antibody described herein (e.g., mAb 1H4);

g) Shows the same or similar binding affinity or specificity, or both, as an antibody molecule comprising an amino acid sequence described herein;

h) Shows the same or similar binding affinity or specificity, or both, as an antibody molecule comprising an amino acid sequence encoded by a nucleotide sequence described herein;

i) Inhibits, e.g., competitively inhibits, the binding of a second antibody molecule to an anti-APRIL antibody (e.g., sibeprenlimab), wherein the second antibody molecule is a monoclonal antibody described herein (e.g., mAb 1H4);

j) Competes for binding with a second antibody molecule to an anti-APRIL antibody (e.g., sibeprenlimab), wherein the second antibody molecule is a monoclonal antibody described herein (e.g., mAb 1H4);

k) Has one or more biological properties of a monoclonal antibody described herein (e.g., mAb 1H4);

l) Has one or more structural properties of a monoclonal antibody described herein (e.g., mAb 1H4); or m) Has one or more pharmacokinetic properties of a monoclonal antibody described herein (e.g., mAb 1H4).

In an aspect, this disclosure provides an isolated antibody molecule capable of binding to an anti-APRIL antibody, e.g., sibeprenlimab, comprising: a heavy chain variable region (VH) comprising the HCDR1 amino acid sequence, the HCDR2 amino acid sequence, and the HCDR3 amino acid sequence of SEQ ID NO: 1; and a light chain variable region (VL) comprising the LCDR1 amino acid sequence, the LCDR2 amino acid sequence, and the LCDR3 amino acid sequence of SEQ ID NO: 2. In an embodiment, the HCDR1 amino acid sequence comprises the amino acid sequence of SEQ ID NO: 11, or an amino acid sequence having no more than 1, 2, or 3 amino acid differences therefrom. In an embodiment, the HCDR2 amino acid sequence comprises the amino acid sequence of SEQ ID NO: 12, or an amino acid sequence having no more than 1, 2, or 3 amino acid differences therefrom. In an embodiment, the HCDR3 amino acid sequence comprises the amino acid sequence of SEQ ID NO: 13, or an amino acid sequence having no more than 1, 2, or 3 amino acid differences therefrom. In an embodiment, the LCDR1 amino acid sequence comprises the amino acid sequence of SEQ ID NO: 14, or an amino acid sequence having no more than 1, 2, or 3 amino acid differences therefrom. In an embodiment, the LCDR2 amino acid sequence comprises the amino acid sequence AAS, or an amino acid sequence having no more than 1, 2, or 3 amino acid differences therefrom. In an embodiment, the LCDR3 amino acid sequence comprises the amino acid sequence of SEQ ID NO: 16, or an amino acid sequence having no more than 1, 2, or 3 amino acid differences therefrom.

In an embodiment, the VH comprises the amino acid sequence of SEQ ID NO: 1, or an amino acid sequence having at least 85%, 90%, 95%, 96%, 97%, 98%, or 99% identity thereto, or differing by no more than 1, 2, 3, 4, 5, 6, 7, 8, 9, 10, 11, 12, 13, 14, or 15 amino acid residues therefrom. In an embodiment, the VH comprises the amino acid sequence of SEQ ID NO: 1.

In an embodiment, the VL comprises the amino acid sequence of SEQ ID NO: 2, or an amino acid sequence having at least 85%, 90%, 95%, 96%, 97%, 98%, or 99% identity thereto, or differing by no more than 1, 2, 3, 4, 5, 6, 7, 8, 9, 10, 11, 12, 13, 14, or 15 amino acid residues therefrom. In an embodiment, the VL comprises the amino acid sequence of SEQ ID NO: 2.

In an embodiment, the VH comprises the amino acid sequence of SEQ ID NO: 1, or an amino acid sequence having at least 85%, 90%, 95%, 96%, 97%, 98%, or 99% identity thereto, or differing by no more than 1, 2, 3, 4, 5, 6, 7, 8, 9, 10, 11, 12, 13, 14, or 15 amino acid residues therefrom; and the VL comprises the amino acid sequence of SEQ ID NO: 2, or an amino acid sequence having at least 85%, 90%, 95%, 96%, 97%, 98%, or 99% identity thereto, or differing by no more than 1, 2, 3, 4, 5, 6, 7, 8, 9, 10, 11, 12, 13, 14, or 15 amino acid residues therefrom. In an embodiment, the VH comprises the amino acid sequence of SEQ ID NO: 1 and the VL comprises the amino acid sequence of SEQ ID NO: 2.

In an embodiment, the antibody molecule comprises two VH and two VL, e.g., two VH and two VL described herein.

In an embodiment, the antibody molecule comprises an antigen-binding fragment. In an embodiment, the antigen-binding fragment comprises a Fab, F(ab')2, Fv, scFv, or sc(Fv)2.

In an embodiment, the antibody molecule comprises a heavy chain constant region of IgG1, IgG2, IgG3, or IgG4. In an embodiment, the antibody molecule comprises a light chain constant region of kappa or lambda light chain. In an embodiment, the antibody molecule comprises a heavy chain constant region of IgG1, IgG2, IgG3, or IgG4; and a light chain constant region of kappa or lambda light chain. In an embodiment, the antibody molecule comprises a heavy chain constant region of IgG1 (e.g., an IgG1 heavy chain constant region described herein) and a light chain constant region of kappa light chain (e.g., a kappa light chain constant region described herein). In an embodiment, the antibody molecule comprises a heavy chain constant region of IgG2 (e.g., an IgG2 heavy chain constant region described herein) and a light chain constant region of kappa light chain (e.g., kappa light chain constant region described herein).

In an embodiment, the antibody molecule comprises an Fc region.

In an embodiment, the antibody molecule comprises a heavy chain comprising amino acids 18-458 of SEQ ID NO: 3. In an embodiment, the antibody molecule comprises a heavy chain comprising amino acids 18-464 of SEQ ID NO: 4. In an embodiment, the antibody molecule comprises a light chain comprising amino acids 18-235 of SEQ ID NO: 5.

In an embodiment, the antibody molecule comprises a heavy chain comprising amino acids 18-458 of SEQ ID NO: 3 and a light chain comprising amino acids 18-235 of SEQ ID NO: 5. In an embodiment, the antibody molecule comprises a heavy chain comprising amino acids 18-464 of SEQ ID NO: 4 and a light chain comprising amino acids 18-235 of SEQ ID NO: 5.

In an embodiment, the antibody molecule comprises a heavy chain comprising the amino acid sequence of SEQ ID NO: 3. In an embodiment, the antibody molecule comprises a heavy chain comprising the amino acid sequence of SEQ ID NO: 4. In an embodiment, the antibody molecule comprises a light chain comprising the amino acid sequence of SEQ ID NO: 5.

In an embodiment, the antibody molecule comprises a heavy chain comprising the amino acid sequence of SEQ ID NO: 3 and a light chain comprising the amino acid sequence of SEQ ID NO: 5. In an embodiment, the antibody molecule comprises a heavy chain comprising the amino acid sequence of SEQ ID NO: 4 and a light chain comprising the amino acid sequence of SEQ ID NO: 5.

In an embodiment, the antibody molecule is mAbs 1H4, 1A5, or 6A3. In an embodiment, the antibody molecule mAb 1H4.

In an embodiment, the antibody molecule is a mouse antibody molecule. In an embodiment, the antibody molecule is a humanized antibody molecule. In an embodiment, the antibody molecule is a monoclonal antibody molecule. In an embodiment, the antibody molecule is a synthetic antibody molecule. In an embodiment, the antibody molecule is a purified antibody molecule, e.g., purified from a hybridoma supernatant, transient transfection of cells (e.g., Expi293 cells), or a stable-expressing cell line (e.g., CHO cells). In an embodiment, the antibody molecule is produced at a concentration of 0.2 mg/mL to 5 mg/mL, e.g., 0.5 mg/mL to 1.5 mg/mL, e.g., from a hybridoma. In an embodiment, the antibody molecule is a ruthenylated-antibody molecule.

In an embodiment, the antibody molecule is an anti-idiotype (anti-ID) antibody molecule. In an embodiment, the antibody molecule binds to one or more (e.g., 2, 3, 4, 5 or 6) CDRs of the anti-APRIL antibody. In an embodiment, the antibody molecule binds to the VH, the VL, or both, of the anti-APRIL antibody. In an embodiment, the antibody molecule does not bind, does not substantially bind, to the Fc region of the anti-APRIL antibody.

In an embodiment, the antibody molecule binds the antibody-APRIL antibody in a binding ELISA assay, e.g., as described herein. In an embodiment, the antibody molecule binds the antibody-APRIL antibody in a bridging ELISA assay, e.g., as described herein. In an embodiment, the antibody molecule binds to the anti-APRIL antibody at an EC50 of less than 500 ng/ml, e.g., less than 400 ng/ml, 300 ng/mL, 200 ng/mL, 150 ng/mL, 120 ng/mL, 100 ng/mL, 90 ng/mL, 80 ng/mL, 70 ng/mL, 60 ng/mL, 50 ng/mL, 40 ng/mL, 35 ng/ml, 30 ng/mL, 25 ng/mL, 20 ng/ml, 15 ng/mL, 10 ng/mL, 5 ng/mL, 2 ng/mL, 1 ng/mL, or 0.1 ng/mL, e.g., 1 ng/mL to 150 ng/mL, 2 ng/ml to 100 ng/mL, 5 ng/ml to 50 ng/mL, or 10 ng/ml to 25 ng/mL, e.g., as determined by ELISA.

In an embodiment, the antibody molecule reduces (e.g., neutralizes, inhibits, or blocks) the binding of the anti-APRIL antibody to APRIL. In an embodiment, the antibody molecule binds to anti-APRIL antibody that is not bound to APRIL. In an embodiment, the antibody molecule does not bind, or does not substantially bind, to anti-APRIL antibody that is bound to APRIL. In an embodiment, the antibody molecule binds to anti-APRIL antibody that is not bound to APRIL, and does not bind, or does not substantially bind, to anti-APRIL antibody that is bound to APRIL. In an embodiment, the antibody molecule binds to anti-APRIL antibody that is not bound to APRIL and anti-APRIL antibody that is bound to APRIL.

In an embodiment, the antibody molecule bridges two anti-APRIL antibodies, e.g., binds to two anti-APRIL antibodies at the same time. In an embodiment, the antibody molecule that competes the anti-APRIL antibody molecule for binding to APRIL.

In an embodiment, the anti-APRIL antibody binds to human APRIL. In an embodiment, the anti-APRIL antibody comprises one or more (e.g., 2, 3, 4, 5, or 6) CDRs of sibeprenlimab. In an embodiment, the anti-APRIL antibody comprises the VH, the VL, or both, of sibeprenlimab. In an embodiment, the anti-APRIL antibody is sibeprenlimab.

In an aspect, the disclosure provides a method of detecting an anti-APRIL antibody, comprising contacting an antibody molecule described herein with a sample; and determining the formation of a complex between the antibody molecule and the sample (e.g., between the antibody molecule and the anti-APRIL antibody in the sample), thereby detecting the anti-APRIL antibody.

In an embodiment, the method further comprises contacting the antibody molecule with a reference sample and determining the formation of a complex between the antibody molecule and the reference sample.

In an embodiment, the anti-APRIL antibody is detected an ELISA assay (e.g., a pharmacokinetic ELISA). In an embodiment, the ELISA is a binding ELISA, e.g., as described herein. In an embodiment, the ELISA is a bridging ELISA, e.g., as described herein. In an embodiment, the anti-APRIL antibody is detected in an anti-drug assay. In an embodiment, the anti-APRIL antibody is detected in a toxicology assay. In an embodiment, the anti-APRIL antibody is detected in a GxP assay.

In an aspect, the disclosure provides a method of evaluating a sample, comprising contacting an antibody molecule described herein with the sample; and determining the formation of a complex between the antibody molecule and the sample (e.g., between the antibody molecule and an anti-APRIL antibody in the sample), thereby evaluating the sample.

In an embodiment, the method further comprises contacting the antibody molecule with a reference sample and determining the formation of a complex between the antibody molecule and the reference sample.

In an embodiment, the sample is evaluated in an ELISA assay (e.g., a pharmacokinetic ELISA). In an embodiment, the ELISA is a binding ELISA, e.g., as described herein. In an embodiment, the ELISA is a bridging ELISA, e.g., as described herein. In an embodiment, the sample is evaluated in an anti-drug assay. In an embodiment, the sample is evaluated in a toxicology assay. In an embodiment, the anti-APRIL antibody is detected in a GxP assay.

In an aspect, the disclosure provides a method of detecting an anti-APRIL antibody, comprising contacting an antibody molecule described herein with (e.g., administering an antibody molecule described herein to) a subject; and determining the formation of a complex between the antibody molecule and the subject (e.g., between the antibody molecule and the anti-APRIL antibody in the subject), thereby detecting the anti-APRIL antibody.

In an aspect, the disclosure provides a method of evaluating a subject, comprising contacting an antibody molecule described herein with (e.g., administering an antibody molecule described herein to) the subject, determining the formation of a complex between the antibody molecule and the subject (e.g., between the antibody molecule and an anti-APRIL antibody in the subject), thereby evaluating the subject.

In an aspect, this disclosure provides an antibody molecule that binds to the same or overlapping epitope as the epitope recognized by an antibody molecule as described herein.

In an aspect, this disclosure provides a composition (e.g., a pharmaceutical composition) comprising an antibody molecule described herein and a pharmaceutically acceptable carrier, excipient or stabilizer. In an embodiment, the composition is suitable for detecting an anti-APRIL antibody in vitro, ex vivo, or in vivo.

In an aspect, the disclosure provides a kit comprising an antibody molecule described herein and instructions to use of the antibody molecule.

In an aspect, this disclosure provides a nucleic acid (e.g., an isolated nucleic acid) encoding one or more (e.g., 2, 3, 4, 5, or 6) CDRs, or the VH, VL, or both, of the antibody molecule described herein.

In an embodiment, the nucleic acid is humanized. In an embodiment, the nucleic acid is codon-optimized.

In an embodiment, the nucleic acid comprises nucleotides 52-1374 of SEQ ID NO: 8, or a nucleotide sequence having at least 85%, 90%, 95%, 96%, 97%, 98%, or 99% identity thereto, or differing by no more than 1, 5, 10, 15, 20, 25, 30, 35, 40, 45, or 50 nucleotides therefrom.

In an embodiment, the nucleic acid comprises nucleotides 52-1392 of SEQ ID NO: 9, or a nucleotide sequence having at least 85%, 90%, 95%, 96%, 97%, 98%, or 99% identity thereto, or differing by no more than 1, 5, 10, 15, 20, 25, 30, 35, 40, 45, or 50 nucleotides therefrom.

In an embodiment, the nucleic acid comprises nucleotides 52-705 of SEQ ID NO: 10, or a nucleotide sequence having at least 85%, 90%, 95%, 96%, 97%, 98%, or 99% identity thereto, or differing by no more than 1, 5, 10, 15, 20, 25, 30, 35, 40, 45, or 50 nucleotides therefrom.

In an embodiment, the nucleic acid comprises nucleotide sequence of SEQ ID NO: 8. In an embodiment, the nucleic acid comprises the nucleotide sequence of SEQ ID NO: 9. In an embodiment, the nucleic acid comprises the nucleotide sequence of SEQ ID NO: 10.

In an aspect, this disclosure provides a vector (e.g., an expression vector) comprising a nucleic acid as described herein. In an embodiment, the expression vector comprises a promoter operably linked to the nucleic acid.

In an aspect, this disclosure provides a cell (e.g., a host cell) comprising a nucleic acid as described herein or a vector as described herein.

In an aspect, this disclosure provides a method of producing an antibody molecule, comprising culturing a host cell as described herein under conditions suitable for gene expression. In an embodiment, the method further comprising isolating or purifying the antibody molecule.

The disclosure contemplates all combinations of any one or more of the foregoing aspects and/or embodiments, as well as combinations with any one or more of the embodiments set forth in the detailed description and examples.

Other features, objects, and advantages of the compositions and methods herein will be apparent from the description and drawings, and from the claims.

DETAILED DESCRIPTION

Figure 1B:
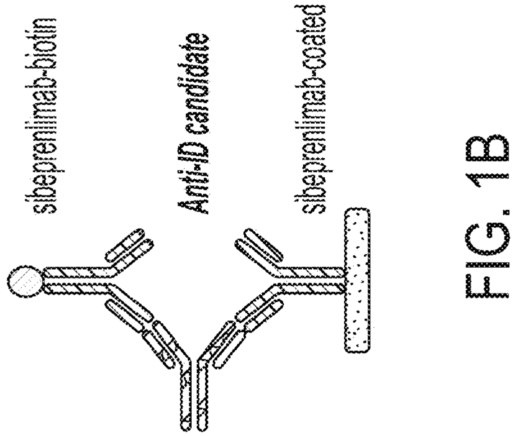
FIGS. 1A-1B depict the binding (FIG. 1A) and bridging (FIG. 1B) ELISA characterization.

Disclosed herein are antibody molecules that bind to an anti-APRIL molecule, e.g., sibeprenlimab, with high affinity and specificity. The production of an anti-idiotype antibody (anti-ID) reagent that specifically recognizes a therapeutic monoclonal antibody (mAb) drug (e.g., sibeprenlimab) is important for creating highly sensitive antibody drug development assays to interrogate preclinical and clinical samples (e.g., pharmacokinetic ELISA, anti-drug assay, and toxicology). The reagents described herein were generated using mouse immunization methods and hybridoma techniques, coupled with extensive screening for a cell line that produces a mAb specific to the variable region of sibeprenlimab. The proper characteristics of an anti-ID mAb can include, for example, specific to the drug's (sibeprenlimab) variable region/CDRs and not the Fc region, negligible cross reactivity to other human or animal immunoglobulins, creates a 'bridge' between two molecules of sibeprenlimab for use in anti-drug assay development, and is easily and reproducibly produced. The anti-ID mAb can be purified, for example, from either: 1) hybridoma supernatant, 2) transient transfection of Expi293 cells, or 3) a stable expressing CHO cell line, whichever provides the most reproducible and high yielding-reagent lots.

Definitions

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% (e.g., within 4%, 3%, 2%, or 1%) of a given value or range of values.

The compositions and methods disclosed herein encompass polypeptides and nucleic acids having the sequences specified, or sequences substantially identical or similar thereto, e.g., sequences at least 80%, 85%, 90%, 91%, 92%, 93%, 94%, 95%, 96%, 97%, 98% or 99% identical or higher to the sequence specified.

In the context of an amino acid sequence, the term "substantially identical" is used herein to refer to a first amino acid that contains a sufficient or minimum number of amino acid residues that are a) identical to, or b) conservative substitutions of aligned amino acid residues in a second amino acid sequence such that the first and second amino acid sequences can have a common structural domain and/or common functional activity. For example, amino acid sequences that contain a common structural domain having at least about 80%, 85%, 90%, 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity or encode a common structural polypeptide domain or a common functional polypeptide activity. For example, nucleotide sequences having at least about 80%, 85%, 90%, 91%, 92%, 93%, 94%, 95%, 96%, 97%, 98% or 99% identity to a reference sequence, e.g., a sequence provided herein.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a typical embodiment, the length of a reference sequence aligned for comparison purposes is at least 30%, e.g., at least 40%, 50%, 60%, 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In an embodiment, the percent identify between two amino acid or nucleotide sequences is determined using Clustal Omega (Sievers et al. *Mol Syst Biol.* 2011; 7:539). In an embodiment, the percent identify between two amino acid or nucleotide sequences is determined using Kalign2 (Lassmann et al. *Nucleic Acids Res.* 2009; 37(3):858-65; Lassmann and Sonnhammer *BMC Bioinformatics.* 2005; 6:298). In an embodiment, the percent identify between two amino acid or nucleotide sequences is determined using MAFFT (Katoh and Standley *Mol Biol Evol.* 2013; 30(4):772-80). In an embodiment, the percent identify between two amino acid or nucleotide sequences is determined using MUSCLE (Edgar *Nucleic Acids Res.* 2004; 32(5):1792-7; Edgar *BMC Bioinformatics.* 2004; 5:113). In an embodiment, the percent identify between two amino acid or nucleotide sequences is determined using MView (Brown et al. Bioinformatics. 1998; 14(4):380-1). Other methods for determining the percent identify between two sequences are also described, e.g., in Li et al. *Nucleic Acids Res.* 2015; 43(W1):W580-4; McWilliam et al. *Nucleic Acids Res.* 2013; 41(Web Server issue):W597-600.

In an embodiment, the percent identity between two amino acid sequences is determined using the Needleman and Wunsch (*J Mol Biol.* 1970; 48(3):443-53) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In an embodiment, the percent identity between two nucleotide sequences is determined using the GAP program in the GCG software package (available at www.gcg.com), using an NWSgapdna. CMP matrix and a gap weight of 40, 50, 60, 70, or 80 and a length weight of 1, 2, 3, 4, 5, or 6. One suitable set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of Meyers and Miller (*Comput Appl Biosci.* 1988; 4(1):11-7) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases, for example, to identify other family members or related sequences. Such searches can be performed using the NBLAST and XBLAST programs (version 2.0) of Altschul, et al. 1990; *J. Mol. Biol.* 215:403-10. BLAST nucleotide searches can be performed with the NBLAST program, score=100, wordlength=12 to obtain nucleotide sequences homologous to a nucleic acid as described herein. BLAST protein searches can be performed with the XBLAST program, score=50, wordlength=3 to obtain amino acid sequences homologous to protein molecules described herein. To obtain gapped alignments for comparison purposes, Gapped BLAST can be utilized as described in Altschul et al., *Nucleic Acids Res.* 1997; 25:3389-3402. When utilizing BLAST and gapped BLAST programs, the default parameters of the respective programs (e.g., XBLAST and NBLAST) can be used. See www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5 M sodium phosphate, 7% SDS at 65° C., followed by one or more washes at 0.2×SSC, 1% SDS at 65° C. Very high stringency conditions 4) are suitable conditions and the ones that should be used unless otherwise specified.

It is understood that the molecules described herein may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide," "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified, for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

As used herein, the term "treat," a disorder, e.g., an APRIL-associated disorder, means that a subject (e.g., a human) who has a disorder, e.g., an APRIL-associated disorder, and/or experiences a symptom of a disorder, e.g., an APRIL-associated disorder, will, in an embodiment, suffer less a severe symptom and/or recover faster when an antibody molecule is administered than if the antibody molecule were never administered. In an embodiment, when an APRIL-associated disorder, is treated, the level of APRIL may be lower in a treated subject compared to a comparable untreated subject. For example, a diagnostic assay using immunofluorescence or electron microscopy will detect APRIL in a biological sample of a subject after administration of an antibody molecule described herein for the effective treatment of the inflammatory disorder. Other assays, e.g., urine tests, blood tests, ultrasound, X-rays, or cystoscopy, can also be used to monitor treatment in a patient, or to detect the presence, e.g., decreased presence (or absence), of a symptom of the disorder, e.g., the APRIL-associated disorder, after treatment of the disorder in the subject. Treatment can, e.g., partially or completely, alleviate, ameliorate, relieve, inhibit, or reduce the severity of, and/or reduce incidence, and optionally, delay onset of, one or more manifestations of the effects or symptoms, features, and/or causes of a disorder, e.g., an APRIL-associated disorder. In an embodiment, treatment is of a subject who does not exhibit certain signs of a disorder, e.g., an APRIL-associated disorder, and/or of a subject who exhibits only early signs of a disorder, e.g., an APRIL-associated disorder. In an embodiment, treatment is of a subject who exhibits one or more established signs of a disorder, e.g., an APRIL-associated disorder. In an embodiment, treatment is of a subject diagnosed as suffering from a disorder, e.g., an APRIL-associated disorder. In an embodiment, the disorder is an APRIL-associated disorder described herein.

As used herein, the term "prevent," a disorder, e.g., an APRIL-associated disorder, means that a subject (e.g., a human) is less likely to have the disorder, e.g., an APRIL-associated disorder, if the subject receives the antibody molecule. In an embodiment, the subject is at risk of developing the disorder, e.g., an APRIL-associated disorder. In an embodiment, the disorder is an APRIL-associated disorder described herein.

Various aspects of the compositions and methods herein are described in further detail below. Additional definitions are set out throughout the specification.

Antibody Molecules

In an aspect, the disclosure provides are antibody molecules (e.g., anti-idiotype antibody molecules) that bind to an anti-APRIL antibody.

As used herein, the term "antibody molecule" refers to a protein, e.g., an immunoglobulin chain or a fragment thereof, comprising at least one immunoglobulin variable domain sequence. The term "antibody molecule" includes, for example, a full-length antibody and an antigen-binding fragment of an antibody.

For example, an antibody molecule can include a heavy (H) chain variable domain sequence (abbreviated herein as VH), and a light (L) chain variable domain sequence (abbreviated herein as VL). In another example, an antibody molecule includes two heavy (H) chain variable domain sequences and two light (L) chain variable domain sequence, thereby forming two antigen binding sites, such as Fab, Fab', F(ab')2, Fc, Fd, Fd', Fv, single chain antibodies (scFv or sc(Fv)2, for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The antibody molecules can be monoclonal or polyclonal. In an embodiment, the antibody molecule is a whole IgG antibody. The antibody molecule can also be a human, humanized, CDR-grafted, or in vitro generated antibody. The antibody molecule can have a heavy chain constant region chosen from, e.g., IgG1, IgG2, IgG3, IgG4, or a chimera of two or more isotypes. The antibody molecule can also have a light chain chosen from, e.g., kappa or lambda. The term "immunoglobulin" (Ig) is used interchangeably with the term "antibody" herein. In an embodiment, the antibody molecule is a multispecific antibody molecule (e.g., a bispecific antibody molecule).

Examples of antigen-binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments may be obtained using any suitable method, including several conventional techniques known to those with skill in the art, and the fragments can be screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

In an embodiment, the antibody molecule is a single chain antibody. A single-chain antibody (scFv) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target protein.

In an embodiment, the antibody molecule is a single domain antibody. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. In an embodiment, a single domain antibody is a naturally occurring single domain antibody known as heavy chain antibody devoid of light chains. Such single domain antibodies are disclosed in WO 94/04678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are also within the scope of the invention.

The VH and VL regions can be subdivided into regions of hypervariability, termed "complementarity determining regions" (CDR), interspersed with regions that are more conserved, termed "framework regions" (FR or FW). The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3). As used herein, the terms "framework," "FW" and "FR" are used interchangeably.

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242 ("Kabat" numbering scheme); Chothia, C. et al. (1987) *J. Mol. Biol.* 196:901-917 ("Chothia" numbering scheme); and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). As used herein, the CDRs defined according the "Chothia" number scheme are also sometimes referred to as "hypervariable loops." Under all definitions, each VH and VL typically includes three CDRs and four FRs, arranged from amino-terminus to carboxy-terminus in the following order: FR1, CDR1, FR2, CDR2, FR3, CDR3, FR4.

For example, under Kabat, the CDR amino acid residues in the heavy chain variable domain (VH) can be numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH can be numbered 26-32 (HCDR1), 52-56 (HCDR2), and 95-102 (HCDR3); and the amino acid residues in VL can be numbered 26-32 (LCDR1), 50-52 (LCDR2), and 91-96 (LCDR3). By combining the CDR definitions of both Kabat and Chothia, the CDRs can consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

Generally, unless specifically indicated, the antibody molecules described herein can include any combination of one or more Kabat CDRs and/or Chothia hypervariable loops as described herein.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids or may include other alterations that are compatible with formation of the protein structure.

The term "antigen-binding region" refers to the part of an antibody molecule that comprises determinants that form an interface that binds to an antigen or an epitope thereof. With respect to proteins (or protein mimetics), the antigen-binding region typically includes one or more loops (of at least, e.g., four amino acids or amino acid mimics) that form an interface that binds to the antigen. Typically, the antigen-binding region of an antibody molecule includes at least one or two CDRs and/or hypervariable loops, or more typically at least three, four, five or six CDRs and/or hypervariable loops.

The terms "compete" or "cross-compete" are used interchangeably herein to refer to the ability of a first antibody molecule to interfere with binding of a second antibody molecule to a target. The interference with binding can be direct or indirect (e.g., through an allosteric modulation of the antibody molecule or the target). The extent to which an antibody molecule is able to interfere with the binding of another antibody molecule to the target, and therefore whether it can be said to compete, can be determined using a competition binding assay, for example, a FACS assay, an ELISA, or a BIACORE assay. In an embodiment, a competition binding assay is a quantitative competition assay. In an embodiment, a first antibody molecule is said to compete for binding to the target with a second antibody molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum and potential allergic reactions (see, e.g., Saleh et al., *Cancer Immunol. Immunother.,* 32:180-190 (1990); LoBuglio et al., *Hybridoma,* 5:5117-5123 (1986)).

The antibody molecule can be a polyclonal or a monoclonal antibody. In an embodiment, the antibody can be recombinantly produced, e.g., produced by any suitable phage display or combinatorial methods.

Various phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In an embodiment, the antibody molecule is a fully human antibody (e.g., an antibody made in a mouse which has been genetically engineered to produce an antibody from a human immunoglobulin sequence), or a non-human antibody, e.g., a rodent (e.g., mouse or rat), goat, primate (e.g., monkey), camel antibody. In an embodiment, the non-human antibody is a rodent (e.g., mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by any suitable recombinant DNA technique. Several are known in the art (see Robinson et al., International Patent Application Publication No. WO1987/002671; Akira, et al., European Patent Application Publication No. 184,187; Taniguchi, M., European Patent Application Publication No. 171,496; Morrison et al., European Patent Application Publication No. 173,494; Neuberger et al., International Patent Application Publication No. WO 86/01533; Cabilly et al. U.S. Pat. No. 4,816,567; Cabilly et al., European Patent Application Publication No. 125,023; Better et al. (1988 *Science* 240:1041-1043); Liu et al. (1987) *PNAS* 84:3439-3443; Liu et al., 1987*, J. Immunol.* 139:3521-3526; Sun et al. (1987) *PNAS* 84:214-218; Nishimura et al., 1987*, Canc. Res.* 47:999-1005; Wood et al. (1985) *Nature* 314:446-449; and Shaw et al., 1988*, J. Natl Cancer Inst.* 80:1553-1559).

A humanized or CDR-grafted antibody will have at least one or two but generally all three recipient CDRs (of heavy and or light immunoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to lipopolysaccharide. In an embodiment, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In an embodiment, the donor immunoglobulin is a non-human (e.g., rodent). The acceptor framework is typically a naturally-occurring (e.g., a human) framework or a consensus framework, or a sequence about 85% or higher, e.g., 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by any suitable method, and several such methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare humanized antibodies (UK Patent Application GB 2188638A, filed on Mar. 26, 1987; Winter U.S. Pat. No. 5,225,539), the contents of which is expressly incorporated by reference.

Also provided are humanized antibodies in which specific amino acids have been substituted, deleted or added. Criteria for selecting amino acids from the donor are described in, e.g., U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

In an embodiment, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody molecule (e.g., to increase or decrease one or more of: Fc receptor binding, antibody glycosylation, the number of cysteine residues, effector cell function, and/or complement function). In an embodiment, the antibody molecule has effector function and can fix complement. In another embodiment, the antibody molecule does not recruit effector cells or fix complement. In an embodiment, the antibody molecule has reduced or no ability to bind an Fc receptor. For example, it may be an isotype or subtype, fragment or other mutant, which does not support binding to an Fc receptor, e.g., it has a mutated or deleted Fc receptor binding region.

In an embodiment, a constant region of the antibody molecule is altered. Methods for altering an antibody constant region are known in the art. Antibody molecules s with altered function, e.g. altered affinity for an effector ligand, such as FcR on a cell, or the C1 component of complement can be produced by replacing at least one amino acid residue in the constant portion of the antibody with a different residue (see, e.g., EP 388,151 A1, U.S. Pat. Nos. 5,624,821 and 5,648,260, the contents of all of which are hereby incorporated by reference). Amino acid mutations which stabilize antibody structure, such as S228P (EU nomenclature, S241P in Kabat nomenclature) in human IgG4 are also contemplated. Similar type of alterations could be described which if applied to the murine, or other species immunoglobulin would reduce or eliminate these functions.

In an embodiment, the only amino acids in the antibody molecule are canonical amino acids. In an embodiment, the antibody molecule comprises naturally-occurring amino acids; analogs, derivatives and congeners thereof; amino acid analogs having variant side chains; and/or all stereoisomers of any of any of the foregoing. The antibody molecule may comprise the D- or L-optical isomers of amino acids and peptidomimetics.

In an embodiment, the antibody molecule comprises a monoclonal antibody (e.g., a full-length antibody which has an immunoglobulin Fc region). In an embodiment, the antibody molecule comprises a full-length antibody or full-length immunoglobulin chain. In an embodiment, the antibody molecule comprises an antigen binding or functional fragment of a full-length antibody or full-length immunoglobulin chain.

In an embodiment, the antibody molecule is a monospecific antibody molecule, e.g., it binds a single epitope. For example, a monospecific antibody molecule can have a plurality of immunoglobulin variable region sequences, each of which binds the same epitope.

In an embodiment, the antibody molecule is a multispecific antibody molecule, e.g., it comprises a plurality of immunoglobulin variable region sequences, wherein a first immunoglobulin variable region sequence of the plurality has binding specificity for a first epitope and a second immunoglobulin variable region sequence of the plurality has binding specificity for a second epitope. In an embodiment, the first and second epitopes are on the same antigen, e.g., the same protein (or subunit of a multimeric protein). In an embodiment, the first and second epitopes overlap. In an embodiment, the first and second epitopes do not overlap. In an embodiment, the first and second epitopes are on different antigens, e.g., the different proteins (or different subunits of a multimeric protein). In an embodiment, a multispecific antibody molecule comprises a third, fourth or fifth immunoglobulin variable domain. In an embodiment, a multispecific antibody molecule is a bispecific antibody molecule, a trispecific antibody molecule, or tetraspecific antibody molecule.

In an embodiment, a multispecific antibody molecule is a bispecific antibody molecule. A bispecific antibody has specificity for no more than two antigens. A bispecific antibody molecule is typically characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment, the first and second epitopes do not overlap. In an embodiment, the first and second epitopes are on different antigens, e.g., the different proteins (or different subunits of a multimeric protein). In an embodiment, a bispecific antibody molecule comprises a heavy chain variable region sequence and a light chain variable region sequence which have binding specificity for a first epitope, and a heavy chain variable region sequence and a light chain variable region sequence which have binding specificity for a second epitope. In an embodiment, a bispecific antibody molecule comprises a half antibody having binding specificity for a first epitope and a half antibody having binding specificity for a second epitope. In an embodiment, a bispecific antibody molecule comprises a half antibody, or a fragment thereof, having binding specificity for a first epitope, and a half antibody, or fragment thereof, having binding specificity for a second epitope. In an embodiment a bispecific antibody molecule comprises an scFv, or a fragment thereof, have binding specificity for a first epitope, and an scFv, or a fragment thereof, have binding specificity for a second epitope.

Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhydryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also disclosed creating bispecific, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with crosslinkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. The contents of the above-referenced applications are incorporated herein by reference in their entirety.

Additional methods of making multispecific or bispecific antibody molecules can be found, for example, in U.S. Pat. Nos. 5,910,573, 5,932,448, 5,959,083, 5,989,830, 6,005,079, 6,239,259, 6,294,353, U.S. Pat. Nos. 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002/004587, US2002/076406, US2002/103345, US2003/207346, US2003/211078, US2004/219643, US2004/220388, US2004/242847, US2005/003403, US2005/004352, US2005/069552, US2005/079170, US2005/100543, US2005/136049, US2005/136051, US2005/163782, US2005/266425, US2006/083747, US2006/120960, US2006/204493, US2006/263367, US2007/004909, US2007/087381, US2007/128150, US2007/141049, US2007/154901, US2007/274985, US2008/050370, US2008/069820, US2008/152645, US2008/171855, US2008/241884, US2008/254512, US2008/260738, US2009/130106, US2009/148905, US2009/155275, US2009/162359, US2009/162360, US2009/175851, US2009/175867, US2009/232811, US2009/234105, US2009/263392, US2009/274649, EP346087, WO00/06605, WO02/072635, WO04/081051, WO06/020258, WO2007/044887, WO2007/095338A2, WO2007/137760A2, WO2008/119353, WO2009/021754, WO2009/068630, WO91/03493, WO93/23537, WO94/09131, WO94/12625, WO95/09917, WO96/37621, WO99/64460. The contents of the above-referenced applications are incorporated herein by reference in their entirety.

A polypeptide of an antibody molecule described herein may be linear or branched, it may comprise modified amino acids, and it may be interrupted by non-amino acids. The antibody molecule may also be modified; for example, by disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The antibody molecule described herein can be used alone in unconjugated form, or can be bound to a substance, e.g., a toxin or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the antibody molecule can be coupled to a radioactive isotope such as an α-, β-, or γ-emitter, or a β- and γ-emitter.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a toxin, a pharmaceutical agent, and/or a protein or peptide that can mediate association of the antibody or antibody portion with another molecule (such as a streptavidin core region or a polyhistidine tag).

Some types of derivatized antibody molecule are produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an anti-dengue antibody molecule may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5dimethylamine-1-naphthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody molecule may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibody molecules can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An antibody molecule described herein can be conjugated to another molecular entity, typically a label or a therapeutic (e.g., antimicrobial (e.g., antibacterial or bactericidal), immunomodulatory, immunostimulatory, cytotoxic, or cytostatic) agent or moiety. Radioactive isotopes can be used in diagnostic or therapeutic applications. Radioactive isotopes that can be coupled to the antibody molecules include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99}$ mTc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{15}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In), technetium ($^{99}$mTc), phosphorus ($^{32}$P), carbon ($^{14}$C), and tritium ($^{3}$H), or one or more of the therapeutic isotopes listed above.

The present disclosure provides radiolabeled antibody molecules and methods of labeling the same. In an embodiment, a method of labeling an antibody molecule is disclosed. The method includes contacting an antibody molecule, with a chelating agent, to thereby produce a conjugated antibody. The conjugated antibody is radiolabeled with a radioisotope, e.g., $^{111}$Indium, $^{90}$Yttrium and $^{177}$Lutetium, to thereby produce a labeled antibody molecule.

In an embodiment, the antibody molecule is conjugated to a therapeutic agent. Therapeutically active radioisotopes are disclosed herein. Examples of other therapeutic agents include, but are not limited to, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see e.g., U.S. Pat. No. 5,208,020), CC-1065 (see e.g., U.S. Pat. Nos. 5,475,092, 5,585,499, 5,846, 545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In an embodiment, the antibody molecule (e.g., a monospecific, bispecific, or multispecific antibody molecule) is covalently linked, e.g., fused, to another partner e.g., a protein, e.g., as a fusion molecule (e.g., a fusion protein).

As used herein, a "fusion protein" and "fusion polypeptide" refer to a polypeptide having at least two portions covalently linked together, where each of the portions is a polypeptide. In an embodiment, each of the portions is a polypeptide that has a different property. The property can be a biological property, such as activity in vitro or in vivo. The property can also be simple chemical or physical property, such as binding to a target molecule, catalysis of a reaction, etc. The two portions can be linked directly by a single peptide bond or through a linker (e.g., peptide linker), but are in reading frame with each other.

In one aspect, the disclosure features a method of providing an antibody molecule that specifically binds to a target protein. The method can include: providing a protein that comprises at least a portion of a target protein, the portion being homologous to (e.g., at least 70, 75, 80, 85, 87, 90, 92, 94, 95, 96, 97, 98% identical to) a corresponding portion of a target protein, but differing by at least one amino acid (e.g., at least one, two, three, four, five, six, seven, eight, or nine amino acids); obtaining an antibody molecule that specifically binds to the target protein; and evaluating efficacy of the antibody molecule in modulating an activity of the target protein. The method can further include contacting the antibody molecule or a derivative with a sample, e.g., from a subject. The method can further include administering the antibody molecule or a derivative to a subject, e.g., a human.

In another aspect, this disclosure provides a method of making an antibody molecule disclosed herein. The method can include: providing an antigen or a fragment thereof; obtaining an antibody molecule that specifically binds to the antigen; evaluating efficacy of the antibody molecule in modulating activity of the antigen and/or organism expressing the antigen. The method can further include contacting the antibody molecule or a derivative with a sample, e.g., from a subject. The method can further include administering the antibody molecule or a derivative to a subject, e.g., a human.

This disclosure provides nucleic acids encoding the antibody molecule described herein, and vectors and host cells including the nucleic acids. The nucleic acids include, but are not limited to, RNA, genomic DNA and cDNA.

Amino acid and nucleotide sequences of exemplary antibody molecules are described below.

Amino acid sequence of 1H4_VH (CDR sequences underlined)

EVRLLQSGGGLVQPGGSLKLSCAASGIDFSRYWMSWVRRAPGQGLEWIGEINPDSSTINYAPSLKDKFIIS

RDNAKKTLYLQMSKVRSEDKVFYYCAIYYDYAMDFWGQGTSVTVSS (SEQ ID NO: 1)

| CDR Sequences for 1H4_VH | Amino Acid Sequence | SEQ ID NO: |
|---|---|---|
| HCDR1 | GIDFSRYW | 11 |
| HCDR2 | INPDSSTI | 12 |
| HCDR3 | AIYYDYAMDF | 13 |

Amino acid sequence of 1H4_Vk (CDR sequences underlined)

DIVLTQSPASLAVSLGQRATISCRASESVDNYGISFMNWFQQKPGQPPKLLIYAASNQGSGVPARFSGSGS

GTDFSLNIHPMEEDDTAMYFCQQNKEVPYTFGGGTKVEIKRT (SEQ ID NO: 2)

| CDR Sequences for 1H4_Vk | Amino Acid Sequence | SEQ ID NO: |
|---|---|---|
| LCDR1 | ESVDNYGISF | 14 |
| LCDR2 | AAS | |
| LCDR3 | QQNKEVPYT | 16 |

Amino acid sequence of 1H4_VH_IgG1 (Osteo Leader: underlined; 1H4_VH: regular; Linker: underlined and italicized; Mouse IgG1 Constant Region: italicized; CDR sequences: bolded and underlined)

MRAWIFFLLCLAGRALAEVRLLQSGGGLVQPGGSLKLSCAASGIDFSRYWMSWVRRAPGQGLEWIGEINPD

SSTINYAPSLKDKFIISRDNAKKTLYLQMSKVRSEDKVFYYCAIYYDYAMDFWGQGTSVTVSS*AKTTPPSV*

*YPLAPGSAAQTNSMVTLGCLVKGYFPEPVTVTWNSGSLSSGVHTFPAVLQSDLYTLSSSVTVPSSTWPSET*

*VTCNVAHPASSTKVDKKIVPRDCGCKPCICTVPEVSSVFIFPPKPKDVLTITLTPKVTCVVVDISKDDPEV*

*QFSWFVDDVEVHTAQTQPREEQFNSTFRSVSELPIMHQDWPNGKEFKCRVNSAAFPAPIEKTISKTKGRPK*

*APQVYTIPPPKEQMAKDKVSLTCMITDFFPEDITVEWQWNGQPAENYKNTQPIMNTNGSYFVYSKLNVQKS*

*NWEAGNTFTCSVLHEGLHNHHTEKSLSHSPGK* (SEQ ID NO: 3)

Amino acid sequence of 1H4_VH_IgG2 (Osteo Leader: underlined; 1H4_VH: regular; Linker: underlined and italicized; Mouse IgG2 Constant Region: italicized; CDR sequences: bolded and underlined)

MRAWIFFLLCLAGRALAEVRLLQSGGGLVQPGGSLKLSCAASGIDFSRYWMSWVRRAPGQGLEWIGEINPD

SSTINYAPSLKDKFIISRDNAKKTLYLQMSKVRSEDKVFYYCAIYYDYAMDFWGQGTSVTVSS*ASTKGPSV*

*YPLAPVCGDTTGSSVTLGCLVKGYFPEPVTLTWNSGSLSSGVHTFPAVLQSDLYTLSSSVTVTSSTWPSQS*

-continued

*ITCNVAHPASSTKVDKKIEPRGPTIKPCPPCKCPAPNLLGGPSVFIFPPKIKDVLMISLSPIVTCVVVDVS*

*EDDPDVQISWFVNNVEVHTAQTQTHREDYNSTLRVVSALPIQHQDWMSGKEFKCKVNNKDLPAPIERTISK*

*PKGSVRAPQVYVLPPPEEEMTKKQVTLTCMVTDFMPEDIYVEWTNNGKTELNYKNTEPVLDSDGSYFMYSK*

*LRVEKKNWVERNSYSCSVVHEGLHNHHTTKSFSRTPGK* (SEQ ID NO: 4)

Amino acid sequence of 1H4_Vk (Osteo Leader: underlined; 1H4_VH: regular; Kappa Constant Region: italicized; CDR sequences: bolded and underlined)

MRAWIFFLLCLAGRALADIVLTQSPASLAVSLGQRATISCRASESVDNYGISFMNWFQQKPGQPPKLLIYA

ASNQGSGVPARFSGSGSGTDFSLNIHPMEEDDTAMYFCQQNKEVPYTFGGGTKVEIKRTDA*APTVSIFPPS*

*SEQLTSGGASVVCFLNNFYPKDINVKWKIDGSERQNGVLNSWTDQDSKDSTYSMSSTLTLTKDEYERHNSY*

*TCEATHKTSTSPIVKSFNRNEC* (SEQ ID NO: 5)

Nucleotide sequence of 1H4_VH (Sequences encoding CDRs bolded and underlined)

GAAGTCAGATTGCTCCAGAGTGGAGGTGGTCTGGTTCAGCCTGGAGGGTCATTGAAACTTTCTTGCGCTGC

ATCAGGCATTGATTTCTCTCGCTACTGGATGTCATGGGTTAGACGCGCTCCCGGTCAAGGTCTGGAGTGGA

TCGGCGAGATAAACCCGGATTCTTCTACCATTAATTACGCACCTAGCCTCAAGGACAAATTTATTATTAGC

CGGGATAATGCAAAAAAGACATTGTACCTCCAGATGTCCAAGGTCAGAAGCGAGGACAAAGTCTTCTACTA

TTGTGCAATTTATTACGATTACGCTATGGACTTCTGGGGACAGGGTACATCTGTTACTGTATCCTCA (SEQ ID NO: 6)

| Sequences encoding CDRs for 1H4_VH | Nucleic Acid Sequence | SEQ ID NO: |
|---|---|---|
| HCDR1 | GGCATTGATTTCTCTCGCTACTGG | 17 |
| HCDR2 | ATAAACCCGGATTCTTCTACCATT | 18 |
| HCDR3 | GCAATTTATTACGATTACGCTATG GACTTC | 19 |

Nucleotide sequence of 1H4_Vk (Sequences encoding CDRs bolded and underlined)

GACATCGTTCTTACGCAATCTCCAGCCTCTTTGGCTGTATCTCTCGGCCAACGAGCGACCATTTCATGTCG

CGCAAGCGAATCAGTAGACAATTACGGTATCTCATTCATGAACTGGTTCCAGCAAAAGCCAGGCCAACCAC

CGAAGCTGTTGATCTACGCAGCATCAAATCAGGGCAGTGGCGTACCAGCACGGTTTTCAGGTAGTGGAAGT

GGGACAGATTTTTCACTCAACATTCATCCTATGGAAGAAGATGATACGGCCATGTACTTTTGCCAGCAAAA

CAAGGAGGTTCCCTATACGTTTGGCGGTGGCACGAAAGTAGAAATAAAGCGTACG (SEQ ID NO: 7)

| Sequences encoding CDRs for 1H4_Vk | Nucleic Acid Sequence | SEQ ID NO: |
|---|---|---|
| LCDR1 | GAATCAGTAGACAATTACGGTATC TCATTC | 20 |
| LCDR2 | GCAGCATCA | |
| LCDR3 | CAGCAAAACAAGGAGGTTCCCTAT ACG | 22 |

Nucleotide sequence of 1H4_VH_IgG1 (Osteo Leader: underlined; 1H4_VH: regular; Linker: underlined and italicized; Mouse IgG1 Constant Region: italicized; CDR-encoding sequences: bolded and underlined)

ATGAGGGCTTGGATCTTCTTTCTGCTCTGCCTGGCCGGGCGCGCCTTGGCCGAAGTCAGATTGCTCCAGAG

TGGAGGTGGTCTGGTTCAGCCTGGAGGGTCATTGAAACTTTCTTGCGCTGCATCAGGCATTGATTTCTCTC

-continued

GCTACTGGATGTCATGGGTTAGACGCGCTCCCGGTCAAGGTCTGGAGTGGATCGGCGAGATAAACCCGGAT

TCTTCTACCATTAATTACGCACCTAGCCTCAAGGACAAATTTATTATTAGCCGGGATAATGCAAAAAAGAC

ATTGTACCTCCAGATGTCCAAGGTCAGAAGCGAGGACAAAGTCTTCTACTATTGTGCAATTTATTACGATT

ACGCTATGGACTTCTGGGGACAGGGTACATCTGTTACTGTATCCTCA*GCCAAAACGACACCCCCATCTGTC*

*TATCCACTGGCCCCTGGATCTGCTGCCCAAACTAACTCTATGGTGACCCTGGGATGCCTGGTCAAGGGCTA*

*TTTCCCTGAGCCAGTGACAGTGACCTGGAACTCTGGCTCCCTGTCCAGCGGTGTGCACACCTTCCCAGCTG*

*TCCTGCAGTCTGACCTCTACACTCTGAGCAGCTCAGTGACTGTCCCCTCCAGCACCTGGCCCAGCGAGACC*

*GTCACCTGCAACGTTGCCCACCCGGCCAGCAGCACCAAGGTGGACAAGAAAATTGTGCCCAGGGATTGTGG*

*TTGTAAGCCTTGCATATGTACAGTCCCAGAAGTATCATCTGTCTTCATCTTCCCCCCAAAGCCCAAGGATG*

*TGCTCACCATTACTCTGACTCCTAAGGTCACGTGTGTTGTGGTAGACATCAGCAAGGATGATCCCGAGGTC*

*CAGTTCAGCTGGTTTGTAGATGATGTGGAGGTGCACACAGCTCAGACGCAACCCCGCGAAGAGCAGTTCAA*

*CAGCACTTTCCGCTCAGTCAGTGAACTTCCCATCATGCACCAGGACTGGCCCAATGGCAAGGAGTTCAAAT*

*GCAGGGTCAACAGCGCAGCTTTCCCTGCCCCCATCGAGAAAACCATCTCCAAAACCAAAGGCAGACCGAAG*

*GCTCCACAGGTGTACACCATTCCACCTCCCAAGGAGCAGATGGCCAAGGATAAAGTCAGTCTGACCTGCAT*

*GATAACAGACTTCTTCCCTGAAGACATTACTGTGGAGTGGCAGTGGAATGGGCAGCCAGCGGAGAACTACA*

*AGAACACTCAGCCCATTATGAACACGAATGGCTCTTACTTCGTCTACAGCAAGCTCAATGTCCAGAAGAGC*

*AACTGGGAGGCAGGAAATACTTTCACCTGCTCTGTGTTACATGAGGGCCTGCATAACCACCATACTGAGAA*

*GAGCCTCTCCCACTCTCCTGGTAAATGATAA* (SEQ ID NO: 8)

Nucleotide sequence of 1H4_VH_IgG2 (Osteo Leader: underlined; 1H4_VH: regular; Linker: underlined and italicized; Mouse IgG2 Constant Region: italicized; CDR-encoding sequences: bolded and underlined)

ATGAGGGCTTGGATCTTCTTTCTGCTCTGCCTGGCCGGGCGCGCCTTGGCCGAAGTCAGATTGCTCCAGAG

TGGAGGTGGTCTGGTTCAGCCTGGAGGGTCATTGAAACTTTCTTGCGCTGCATCAGGCATTGATTTCTCTC

GCTACTGGATGTCATGGGTTAGACGCGCTCCCGGTCAAGGTCTGGAGTGGATCGGCGAGATAAACCCGGAT

TCTTCTACCATTAATTACGCACCTAGCCTCAAGGACAAATTTATTATTAGCCGGGATAATGCAAAAAAGAC

ATTGTACCTCCAGATGTCCAAGGTCAGAAGCGAGGACAAAGTCTTCTACTATTGTGCAATTTATTACGATT

ACGCTATGGACTTCTGGGGACAGGGTACATCTGTTACTGTATCCTCA*GCCTCCACCAAGGGCCCATCGGTC*

*TATCCACTGGCCCCTGTGTGTGGAGATACAACTGGCTCCTCGGTGACTCTAGGATGCCTGGTCAAGGGTTA*

*TTTCCCTGAGCCAGTGACCTTGACCTGGAACTCTGGATCCCTGTCCAGTGGTGTGCACACCTTCCCAGCTG*

*TCCTGCAGTCTGACCTCTACACCCTCAGCAGCTCAGTGACTGTAACCTCGAGCACCTGGCCCAGCCAGTCC*

*ATCACCTGCAATGTGGCCCACCCGGCAAGCAGCACCAAGGTGGACAAGAAAATTGAGCCCAGAGGCCCCAC*

*AATCAAGCCCTGTCCTCCATGCAAATGCCCAGCACCTAACCTCTTGGGTGGACCATCCGTCTTCATCTTCC*

*CTCCAAAGATCAAGGATGTACTCATGATCTCCCTGAGCCCCATAGTCACATGTGTGGTGGTGGATGTGAGC*

*GAGGATGACCCAGATGTCCAGATCAGCTGGTTTGTGAACAACGTGGAAGTACACACAGCTCAGACACAAAC*

*CCATAGAGAGGATTACAACAGTACTCTCCGGGTGGTCAGTGCCCTCCCCATCCAGCACCAGGACTGGATGA*

*GTGGCAAGGAGTTCAAATGCAAGGTCAACAACAAAGACCTCCCAGCGCCCATCGAGAGAACCATCTCAAAA*

*CCCAAAGGGTCAGTAAGAGCTCCACAGGTATATGTCTTGCCTCCACCAGAAGAAGAGATGACTAAGAAACA*

*GGTCACTCTGACCTGCATGGTCACAGACTTCATGCCTGAAGACATTTACGTGGAGTGGACCAACAACGGGA*

*AAACAGAGCTAAACTACAAGAACACTGAACCAGTCCTGGACTCTGATGGTTCTTACTTCATGTACAGCAAG*

-continued

*CTGAGAGTGGAAAAGAAGAACTGGGTGGAAAGAAATAGCTACTCCTGTTCAGTGGTCCACGAGGGTCTGCA*

*CAATCACCACACGACTAAGAGCTTCTCCCGGACTCCGGGTAAATGATAA* (SEQ ID NO: 9)

Nucleotide sequence of 1H4_Vk (Osteo Leader: underlined; 1H4_VH: regular; Kappa Constant Region: italicized; CDR-encoding sequences: bolded and underlined)

ATGAGGGCTTGGATCTTCTTTCTGCTCTGCCTGGCCGGGCGCGCCCTTGCCGACATCGTTCTTACGCAATC

TCCAGCCTCTTTGGCTGTATCTCTCGGCCAACGAGCGACCATTTCATGTCGCGCAAGCGAATCAGTAGACA

ATTACGGTATCTCATTCATGAACTGGTTCCAGCAAAAGCCAGGCCAACCACCGAAGCTGTTGATCTACGCA

GCATCAAATCAGGGCAGTGGCGTACCAGCACGGTTTTCAGGTAGTGGAAGTGGGACAGATTTTTCACTCAA

CATTCATCCTATGGAAGAAGATGATACGGCCATGTACTTTTGCCAGCAAAACAAGGAGGTTCCCTATACGT

TTGGCGGTGGCACGAAAGTAGAAATAAAGCGTACG*GATGCTGCACCAACTGTATCCATCTTCCCACCATCC*

*AGTGAGCAGTTAACATCTGGAGGTGCCTCAGTCGTGTGCTTCTTGAACAACTTCTACCCCAAAGACATCAA*

*TGTCAAGTGGAAGATTGATGGCAGTGAACGACAAAATGGCGTCCTGAACAGTTGGACTGATCAGGACAGCA*

*AAGACAGCACCTACAGCATGAGCAGCACCCTCACGTTGACCAAGGACGAGTATGAACGACATAACAGCTAT*

*ACCTGTGAGGCCACTCACAAGACATCAACTTCACCCATTGTCAAGAGCTTCAACAGGAATGAGTGTTGATA*

*A* (SEQ ID NO: 10)

In an embodiment, the antibody molecule comprises one, two, or three CDRs of the VH region of a monoclonal antibody described herein (e.g., any of monoclonal antibodies 1H4, 1A5, 6A3, 1B8, 1E5, 6C1, 3F4, 6C12, 2F5, or 6H5), using the Kabat or Chothia definitions of CDRs. In an embodiment, the antibody molecule comprises one, two, or three CDRs of the VL region of a monoclonal antibody described herein (e.g., any of monoclonal antibodies 1H4, 1A5, 6A3, 1B8, 1E5, 6C1, 3F4, 6C12, 2F5, or 6H5), using the Kabat or Chothia definitions of CDRs. In an embodiment, the antibody molecule comprises one or more (e.g., two or three) CDRs of the VH region and/or one or more (e.g., two or three) CDRs of the VL region of a monoclonal antibody described herein (e.g., any of monoclonal antibodies 1H4, 1A5, 6A3, 1B8, 1E5, 6C1, 3F4, 6C12, 2F5, or 6H5), using the Kabat or Chothia definitions of CDRs.

In an embodiment, the antibody molecule comprises one, two, or three VH CDRs described herein. In an embodiment, the antibody molecule comprises one, two, or three VL CDRs described herein. In an embodiment, the antibody molecule comprises one or more (e.g., two or three) VH CDRs and/or one or more (e.g., two or three) VL CDRs described herein.

In an embodiment, the antibody molecule comprises one, two, or three VH CDRs comprising the amino acid sequence of SEQ ID NOs: 11, 12, and/or 13, or amino acid sequences having no more than 1, 2, or 3 amino acid differences therefrom. In an embodiment, the antibody molecule comprises a set of three VH CDRs comprising the amino acid sequence of SEQ ID NOs: 11, 12, and 13, or amino acid sequences having no more than 1, 2, or 3 amino acid differences therefrom. In an embodiment, the antibody molecule comprises one, two, or three VH CDRs comprising the amino acid sequence of SEQ ID NOs: 11, 12, and/or 13. In an embodiment, the antibody molecule comprises a set of three VH CDRs comprising the amino acid sequence of SEQ ID NOs: 11, 12, and 13.

In an embodiment, the antibody molecule comprises one, two, or three VL CDRs comprising the amino acid sequence of SEQ ID NO: 14, AAS, and/or SEQ ID NO: 16, or amino acid sequences having no more than 1, 2, or 3 amino acid differences therefrom. In an embodiment, the antibody molecule comprises a set of three VL CDRs comprising the amino acid sequence of SEQ ID NO: 14, AAS, and SEQ ID NO: 16, or amino acid sequences having no more than 1, 2, or 3 amino acid differences therefrom. In an embodiment, the antibody molecule comprises one, two, or three VL CDRs comprising the amino acid sequence of SEQ ID NO: 14, AAS, and/or SEQ ID NO; 16. In an embodiment, the antibody molecule comprises a set of three VL CDRs comprising the amino acid sequence of SEQ ID NO: 14, AAS, and SEQ ID NO: 16.

In an embodiment, the antibody molecule comprises one, two, or three VH CDRs comprising amino acid sequences encoded by SEQ ID NOs: 17, 18, and/or 19, or nucleic acid sequences having no more than 1, 2, 3, 4, 5, 6, 7, 8, 9, or 10 nucleotide differences therefrom. In an embodiment, the antibody molecule comprises a set of three VH CDRs comprising CDR sequences encoded by SEQ ID NOs: 17, 18, and 19, or nucleic acid sequences having no more than 1, 2, 3, 4, 5, 6, 7, 8, 9, or 10 nucleotide differences therefrom. In an embodiment, the antibody molecule comprises one, two, or three VH CDRs comprising amino acid sequences encoded by SEQ ID NOs: 17, 18, and/or 19. In an embodiment, the antibody molecule comprises a set of three VH CDRs comprising CDR sequences encoded by SEQ ID NOs: 17, 18, and 19.

In an embodiment, the antibody molecule comprises one, two, or three VL CDRs comprising amino acid sequences encoded by SEQ ID NOs: 20, 21, and/or 22, or nucleic acid sequences having no more than 1, 2, 3, 4, 5, 6, 7, 8, 9, or 10 nucleotide differences therefrom. In an embodiment, the antibody molecule comprises a set of three VL CDRs comprising CDR sequences encoded by SEQ ID NOs: 20, 21, and 22, or nucleic acid sequences having no more than 1, 2, 3, 4, 5, 6, 7, 8, 9, or 10 nucleotide differences therefrom. In an embodiment, the antibody molecule comprises one, two, or three VL CDRs comprising amino acid sequences encoded by SEQ ID NOs: 20, 21, and/or 22. In an embodiment, the antibody molecule comprises a set of three VL CDRs comprising CDR sequences encoded by SEQ ID NOs: 20, 21, and 22.

In an embodiment, the antibody molecule comprises one, two, three, or four frameworks of the VH region of a monoclonal antibody described herein (e.g., any of monoclonal antibodies 1H4, 1A5, 6A3, 1B8, 1E5, 6C1, 3F4, 6C12, 2F5, or 6H5). In an embodiment, the antibody molecule comprises one, two, three, or four frameworks of the VL region of a monoclonal antibody described herein (e.g., any of monoclonal antibodies 1H4, 1A5, 6A3, 1B8, 1E5, 6C1, 3F4, 6C12, 2F5, or 6H5). In an embodiment, the antibody molecule comprises one or more (e.g., two, three, or four) frameworks of the VH region and/or one or more (e.g., two, three, or four) frameworks of the VL region of a monoclonal antibody described herein (e.g., any of monoclonal antibodies 1H4, 1A5, 6A3, 1B8, 1E5, 6C1, 3F4, 6C12, 2F5, or 6H5).

In an embodiment, the antibody molecule comprises a heavy chain variable region of a monoclonal antibody described herein (e.g., any of monoclonal antibodies 1H4, 1A5, 6A3, 1B8, 1E5, 6C1, 3F4, 6C12, 2F5, or 6H5). In an embodiment, the antibody molecule comprises a light chain variable region of a monoclonal antibody described herein (e.g., any of monoclonal antibodies 1H4, 1A5, 6A3, 1B8, 1E5, 6C1, 3F4, 6C12, 2F5, or 6H5). In an embodiment, the antibody molecule comprises a heavy chain variable region and a light chain variable region of a monoclonal antibody described herein (e.g., any of monoclonal antibodies 1H4, 1A5, 6A3, 1B8, 1E5, 6C1, 3F4, 6C12, 2F5, or 6H5).

In an embodiment, the antibody molecule comprises a heavy chain variable region having an amino acid sequence described herein, or an amino acid sequence substantially identical thereof. In an embodiment, the antibody molecule comprises a light chain variable region having an amino acid sequence described herein, or an amino acid sequence substantially identical thereof. In an embodiment, the antibody molecule comprises a heavy chain variable region having an amino acid sequence described herein (or an amino acid sequence substantially identical thereof) and a light chain variable region having an amino acid sequence described herein.

In an embodiment, the antibody molecule comprises a heavy chain having an amino acid sequence described herein, or an amino acid sequence substantially identical thereof. In an embodiment, the antibody molecule comprises a light chain having an amino acid sequence described herein, or an amino acid sequence substantially identical thereof. In an embodiment, the antibody molecule comprises a heavy chain having an amino acid sequence described herein (or an amino acid sequence substantially identical thereof) and a light chain having an amino acid sequence described herein.

In an embodiment, the antibody molecule comprises a heavy chain variable region encoded by a nucleotide sequence described herein, or a nucleotide sequence substantially identical thereof. In an embodiment, the antibody molecule comprises a light chain variable region encoded by a nucleotide sequence described herein, or a nucleotide sequence substantially identical thereof. In an embodiment, the antibody molecule comprises a heavy chain variable region encoded by a nucleotide sequence described herein (or a nucleotide sequence substantially identical thereof) and a light chain variable region encoded by a nucleotide sequence described herein (or a nucleotide sequence substantially identical thereof).

In an embodiment, the antibody molecule further comprises a heavy chain constant region. In an embodiment, the heavy chain constant region is an IgG1 constant region or a functional portion thereof. In another embodiment, the heavy chain constant region is an IgG2 constant region or a functional portion thereof. In an embodiment, the antibody molecule further comprises a light chain constant region. In an embodiment, the antibody molecule further comprises a heavy chain constant region. In an embodiment, the heavy chain constant region is an IgG3 constant region or a functional portion thereof. In an embodiment, the antibody molecule further comprises a heavy chain constant region. In an embodiment, the heavy chain constant region is an IgG4 constant region or a functional portion thereof. In an embodiment, the antibody molecule further comprises a heavy chain constant region and a light chain constant region. In an embodiment, the antibody molecule comprises a heavy chain constant region, a light chain constant region, and heavy and light chain variable regions of a monoclonal antibody described herein (e.g., any of monoclonal antibodies 1H4, 1A5, 6A3, 1B8, 1E5, 6C1, 3F4, 6C12, 2F5, or 6H5). In an embodiment, the antibody molecule comprises a heavy chain constant region, a light chain constant region, and variable regions that comprise one, two, three, four, five, or six CDRs of a monoclonal antibody described herein (e.g., any of monoclonal antibodies 1H4, 1A5, 6A3, 1B8, 1E5, 6C1, 3F4, 6C12, 2F5, or 6H5).

In an embodiment, the antibody molecule further comprises a linker, e.g., a linker described herein. In an embodiment, the antibody molecule further comprises a leader, e.g., a leader described herein.

APRIL

APRIL (A PRoliferation Inducing Ligand), also known as CD256, TNF- and APOL-related Leukocyte Expressed Ligand 2 (TALL-2), or TNF-related Death Ligand 1 (TRDL-1), is a TNF family cytokine encoded by the Tumor Necrosis Factor Ligand Superfamily Member 13 (TNFSF13) gene (also known as APRIL, TALL2, or ZTNF2). APRIL plays a role in a number of biological processes such as signal transduction, regulation of cell proliferation, and IgA class switching (Hahne et al. (1998) *J. Exp. Med.* 188:1185-1190 (1998); Castigli et al. *Proc. Natl. Acad. Sci. U.S.A.* 101: 3903-3908 (2004)).

APRIL is both functionally and structurally related to BAFF (B Cell Activating Factor F13B) also known as BLyS (B lymphocyte stimulator). Both cytokines are involved in regulating keys aspects of innate and adaptive immune functions. Both APRIL and BAFF bind the lymphocyte receptors TACI (transmembrane activator and CAML interactor) and BCMA (B cell maturation antigen). APRIL and BAFF appear to heterologously interact with each other through protein-protein interactions. While both APRIL and BAFF share biochemical (receptor binding), immunological and even some structural overlap (e.g., as it relates to the three-dimensional topology of their respective receptor binding domains), the two cytokines, nevertheless, are both structurally and functionally distinct. APRIL binds to biologically relevant heparan sulfate (present in the extracellular matrices of cells as heparan sulfate proteoglycans); BAFF does not. This interaction plays a critical biological function with respect to promoting the oligomerization state of APRIL in concert with its localized interaction with TACI, which likewise requires HSPGS for full activity. Unlike BAFF which acts as a potent activator of B cells inclusive of both proliferation and differentiation, APRIL would appear to function more particularly with respect to the modulation of B cell phenotype, e.g., as it relates to IgA production and the differentiation/survival of IgA positive plasma cells. As such, a targeted disruption in APRIL-receptor signaling is expected to have less perturbative effects on B cell homeostasis and overall immune function in comparison to other immune related therapeutics that target BAFF (e.g., belimumab) or anti CD20 therapies (e.g., rituximab) that largely target pre and early B cells. APRIL has also been shown to be expressed at high levels on other myeloid related cells and lymphoid tissues, as well as hematological cancers (e.g., myeloma, chronic lymphocytic leukemia (CLL)) and solid tumors (e.g., colon, thyroid, and breast).

Exemplary amino acid and nucleotide sequences of human APRIL are described, e.g., in Hahne et al. *J. Exp. Med.* 188:1185-1190 (1998); Shu et al. *J. Leukoc. Biol.* 65:680-683 (1999); Kelly et al. *Cancer Res.* 60:1021-1027 (2000); and Pradet-Balade et al. *EMBO J.* 21:5711-5720 (2002). Other variant and alternative sequences of human APRIL are described, e.g., in The MGC Project Team, *Genome Res.* 14:2121-2127 (2004); Ota et al. *Nat. Genet.* 36:40-45 (2004); and Kelly et al. *Cancer Res.* 60:1021-1027 (2000). Exemplary amino acid and nucleotide sequences of human and mouse APRIL are also described, e.g., in International Application Publication No. WO2017/091683, the content of which is incorporated by reference in its entirety.

Animal Models

The antibody molecules described herein can be evaluated in vivo, e.g., using various animal models. For example, an animal model can be used to test the pharmacokinetic and/or pharmacodynamics properties of an antibody molecule described herein.

Exemplary animal models for IgA nephropathy that can be used for evaluating an antibody molecule described herein include, but are not limited to, a ddY mouse model for spontaneous IgA nephritis (Imai et al. *Kidney Int.* 1985; 27(5):756-761); a mouse model utilizing inert proteins or a common viral pathogen as the inciting antigen (Emancipator et al. *Curr. Protoc. Immunol.* 2001 May; Chapter 15: Unit 15.11), a rat model by noninfectious protein antigens (Emancipator et al. *Curr. Protoc. Immunol.* 2001 May; Chapter 15: Unit 15.11); a chronic mouse model of IgA immune-complex-associated nephropathy (Montinaro et al. *Nephrol. Dial. Transplant.* 1995; 10(11):2035-2042); the Gne M712T mouse as a model for human glomerulopathy (Kakani et al. *Am. J. Pathol.* 2012; 180(4):1431-1440); a mouse IgA nephropathy model with the MBP-20-peptide fusion protein (Zhang et al. *Anat. Rec.* (*Hoboken*). 2010; 293(10):1729-1737); and a mouse model for IgA immune complex nephritis (Rifai et al. *J Exp Med.* 1979; 150(5):1161-1173). Other animal models for IgA nephropathy are described, e.g., in Tomino et al. *J. Nephrol.* 2008; 21(4):463-467; Endo Ren. Fail. 1997; 19(3):347-371; and Rifai *Kidney Int.* 1987; 31(1):1-7.

Exemplary animal models for other disorders described herein are also known in the art. Exemplary types of animals that can be used to evaluate the antibody molecules described herein include, but are not limited to, mice, rats, rabbits, guinea pigs, and monkeys.

Compositions

The antibody molecules described herein can be included in a composition. In an embodiment, the composition is a pharmaceutical composition, e.g., comprising a pharmaceutically acceptable carrier. The compositions described herein can be used in assays for evaluating an anti-APRIL antibody molecule in a sample or subject.

As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g., by injection or infusion). In an embodiment, less than about 5%, e.g., less than about 4%, 3%, 2%, or 1% of the antibody molecules in the pharmaceutical composition are present as aggregates. In other embodiments, at least about 95%, e.g., at least about 96%, 97%, 98%, 98.5%, 99%, 99.5%, 99.8%, or more of the antibody molecules in the pharmaceutical composition are present as monomers. In an embodiment, the level of aggregates or monomers is determined by chromatography, e.g., high performance size exclusion chromatography (HP-SEC).

The compositions set out herein may be in a variety of forms. These include, for example, liquid, semi-solid and solid dosage forms, such as liquid solutions (e.g., injectable and infusible solutions), dispersions or suspensions, liposomes, and suppositories. A suitable form depends on the intended mode of administration and therapeutic application. Typical suitable compositions are in the form of injectable or infusible solutions. One suitable mode of administration is parenteral (e.g., intravenous, subcutaneous, intraperitoneal, intramuscular). In an embodiment, the antibody molecule is administered by intravenous infusion or injection. In an embodiment, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibody molecules described herein can be administered by a variety of methods. Several are known in the art, and for many therapeutic, prophylactic, or diagnostic applications, an appropriate route/mode of administration is intravenous injection or infusion. For example, the antibody molecules can be administered by intravenous infusion at a rate of less than 10 mg/min; preferably less than or equal to 5 mg/min to reach a dose of about 1 to 100 mg/m$^2$, preferably about 5 to 50 mg/m$^2$, about 7 to 25 mg/m$^2$ and more preferably, about 10 mg/m$^2$. As will be appreciated by the skilled artisan, the route and/or mode of administration will vary depending upon the desired results. In an embodiment, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In an embodiment, an antibody molecule can be orally administered, for example, with an inert diluent or an assimilable edible carrier. The antibody molecule (and other ingredients, if desired) may also be enclosed in a hard or soft shell gelatin capsule, compressed into tablets, or incorporated directly into the subject's diet. For oral therapeutic administration, the antibody molecule may be incorporated with excipients and used in the form of ingestible tablets, buccal tablets, troches, capsules, elixirs, suspensions, syrups, wafers, and the like. To administer an antibody molecule by other than parenteral administration, it may be necessary to coat the compound with, or co-administer the compound with, a material to prevent its inactivation. Therapeutic, prophylactic, or diagnostic compositions can also be administered with medical devices, and several are known in the art.

Dosage regimens are adjusted to provide the desired response (e.g., a therapeutic, prophylactic, or diagnostic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the antibody molecule and the particular therapeutic, prophylactic, or diagnostic effect to be achieved, and (b) the limitations inherent in the art of compounding such an antibody molecule for the treatment of sensitivity in individuals.

An exemplary, non-limiting range for a therapeutically, prophylactically, or diagnostically effective amount of an antibody molecule is about 0.1-50 mg/kg body weight of a subject, e.g., about 0.1-30 mg/kg, e.g., about 1-30, 1-15, 1-10, 1-5, 5-10, or 1-3 mg/kg, e.g., about 1, 2, 3, 4, 5, 6, 7, 8, 9, 10, 15, 20, 30, 40, or 50 mg/kg. The antibody molecule can be administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, e.g., about 10 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed compositions.

The pharmaceutical compositions herein may include a "therapeutically effective amount," "prophylactically effective amount," or "diagnostically effectively amount" of an antibody molecule described herein.

A "therapeutically effective amount" refers to an amount effective, at dosages and for periods of time necessary, to achieve the desired therapeutic result. A therapeutically effective amount of the antibody molecule may vary according to factors such as the disease state, age, sex, and weight of the individual, and the ability of the antibody or antibody portion to elicit a desired response in the individual. A therapeutically effective amount is also one in which any toxic or detrimental effect of the antibody molecule is outweighed by the therapeutically beneficial effects. A "therapeutically effective dosage" typically inhibits a measurable parameter by at least about 20%, e.g., by at least about 40%, by at least about 60%, or by at least about 80% relative to untreated subjects. The measurable parameter may be, e.g., hematuria, colored urine, foamy urine, pain, swelling (edema) in the hands and feet, or high blood pressure. The ability of an antibody molecule to inhibit a measurable parameter can be evaluated in an animal model system predictive of efficacy in treating or preventing a disorder. Alternatively, this property of a composition can be evaluated by examining the ability of the antibody molecule to inhibit a measurable parameter in an in vitro or ex vivo assay.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A "diagnostically effective amount" refers to an amount effective, at dosages and for periods of time necessary, to achieve the desired diagnostic result. Typically, a diagnostically effective amount is one in which a disorder can be diagnosed in vitro, ex vivo, or in vivo.

Kits

The antibody molecules described herein can be included in kits.

The kit can include one or more other elements including: instructions for use; other reagents, e.g., a label, a therapeutic agent, or an agent useful for chelating, or otherwise coupling, an antibody molecule to a label or therapeutic agent, or a radioprotective composition; devices or other materials for preparing the antibody molecule for administration; pharmaceutically acceptable carriers; and devices or other materials for administration to a subject.

Nucleic Acids

The disclosure provides nucleic acids comprising a nucleotide sequence (e.g., a nucleotide sequence described herein) that encodes an antibody molecule described herein or a functional fragment thereof (e.g., a VH, a VL, or both).

For example, the present disclosure features a first and second nucleic acid encoding heavy and light chain variable regions, respectively, of an antibody molecule described herein, or a portion of an antibody molecule described herein. The nucleic acid can comprise a nucleotide sequence encoding an amino acid sequence described herein, or a nucleotide sequence substantially identical thereto (e.g., a nucleotide sequence at least about 85%, 90%, 95%, 99% or more identical thereto, or which differs by no more than 3, 6, 15, 30, or 45 nucleotides therefrom).

In an embodiment, the nucleic acid comprises a nucleotide sequence encoding at least one, two, or three CDRs from a heavy chain variable region having an amino acid sequence described herein (e.g., CDRs comprising the amino acid sequences of SEQ ID NOs: 11, 12, and/or 13), or an amino acid sequence substantially identical thereto (e.g., an amino acid sequence at least about 85%, 90%, 95%, 99% or more identical thereto, and/or having one or more substitutions, e.g., conserved substitutions). In an embodiment, the nucleic acid comprises a nucleotide sequence encoding at least one, two, or three CDRs from a light chain variable region having an amino acid sequence described herein (e.g., CDRs comprising the amino acid sequences of SEQ ID NO: 14, AAS, and/or SEQ ID NO: 16), or an amino acid sequence substantially identical thereto (e.g., a sequence at least about 85%, 90%, 95%, 99% or more identical thereto, and/or having one or more substitutions, e.g., conserved substitutions). In an embodiment, the nucleic acid comprises a nucleotide sequence encoding at least one, two, or three CDRs from a heavy chain variable region having an amino acid sequence described herein (e.g., CDRs comprising the amino acid sequences of SEQ ID NOs: 11, 12, and/or 13), or an amino acid sequence substantially identical thereto (e.g., an amino acid sequence at least about 85%, 90%, 95%, 99% or more identical thereto, and/or having one or more substitutions, e.g., conserved substitutions); and a nucleotide sequence encoding at least one, two, or three CDRs from a light chain variable region having an amino acid sequence described herein (e.g., CDRs comprising the amino acid sequences of SEQ ID NO: 14, AAS, and/or SEQ ID NO: 16), or an amino acid sequence substantially identical thereto (e.g., a sequence at least about 85%, 90%, 95%, 99% or more identical thereto, and/or having one or more substitutions, e.g., conserved substitutions).

In an embodiment, the nucleic acid comprises a nucleotide sequence described herein or a nucleotide sequence substantially homologous thereto (e.g., a nucleotide sequence at least about 85%, 90%, 95%, 99% or more identical thereto, and/or capable of hybridizing under the stringency conditions described herein). In an embodiment, the nucleic acid comprises a portion (e.g., a functional portion) of a nucleotide sequence described herein or a sequence substantially homologous thereto (e.g., a nucleotide sequence at least about 85%, 90%, 95%, 99% or more identical thereto, and/or capable of hybridizing under the stringency conditions described herein). The portion may encode, for example, a variable region (e.g., VH or VL); one, two, or three or more CDRs; or one, two, three, or four or more framework regions.

The nucleic acids described herein include deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The nucleic acids described herein can be included in vectors and host cells. The nucleic acids may be present in a single vector or separate vectors, present in the same host cell or separate host cell, as described in more detail below.

Vectors

The disclosure provides vectors (e.g., cloning vectors and expression vectors) that comprise a nucleic acid described herein.

In an embodiment, the vector comprises a nucleic acid comprising a nucleotide sequence encoding an antibody molecule described herein. In another embodiment, the vector comprises a nucleic acid comprising a nucleotide sequence described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed or introduced into the same cell by cotransformation. Additional elements may also be needed for optimal synthesis of mRNA. These elements may include splice signals, as well as transcriptional promoters, enhancers, and termination signals.

Once the vector has been prepared for expression, the vector may be transfected or introduced into an appropriate host cell. Various techniques may be employed to achieve this, such as, for example, protoplast fusion, calcium phosphate precipitation, electroporation, retroviral transduction, viral transfection, gene gun, lipid-based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art and may be varied or optimized depending upon the specific expression vector and mammalian host cell employed, based upon the present description.

Cells

The disclosure provides cells (e.g., host cells) that comprise a nucleic acid described herein or a vector described herein.

In an embodiment, the cell is genetically engineered to comprise a nucleic acid described herein or a vector described herein. In an embodiment, the cell is genetically engineered using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells. In an embodiment, the cell (e.g., host cell) is an isolated cell.

Uses of Antibody Molecules

The antibody molecules disclosed herein, as well as the compositions disclosed herein, have in vitro, ex vivo, and in vivo utilities.

In an embodiment, the antibody molecule reduces (e.g., inhibits, blocks, or neutralizes) one or more biological activities of an anti-APRIL antibody (e.g., sibeprenlimab). For example, these antibodies molecules can be administered to cells in culture, in vitro or ex vivo, or to a subject, e.g., a human subject, e.g., in vivo, to reduce (e.g., inhibits, blocks, or neutralizes) one or more biological activities of the anti-APRIL antibody. In an embodiment, the antibody molecule competes the anti-APRIL antibody for binding to APRIL. In an embodiment, the antibody molecule inhibits, or substantially inhibit, binding of the anti-APRIL antibody to APRIL. Accordingly, in an aspect, the disclosure provides a method of evaluating a subject, or a sample from a subject, who has been treated with an anti-APRIL antibody, comprising contacting the sample or subject with an antibody molecule described herein, such that the sample or subject is evaluated.

As used herein, the term "subject" is intended to include human and non-human animals. In an embodiment, the subject is a human subject, e.g., a human patient having an APRIL-associated disorder, or at risk of having an APRIL-associated disorder. In an embodiment, the APRIL-associated disorder is IgA nephropathy. The term "non-human animals" includes mammals and non-mammals, such as non-human primates. In an embodiment, the subject is a human. The antibody molecules described herein are suitable for determining the level or activity of an anti-APRIL antibody in the subject. Subjects having an APRIL-associated disorder include, for example, those who have developed an APRIL-associated disorder, but are (at least temporarily) asymptomatic, subjects who have exhibited a symptom of an APRIL-associated disorder, or subjects having a disorder related to an APRIL-associated disorder.

Methods of Diagnosis

The disclosure provides diagnostic methods for detecting the presence of an anti-APRIL antibody in vitro (e.g., in a sample, such as a blood sample or biopsy) or in vivo (e.g., in vivo imaging in a subject). The method includes: (i) contacting the sample with an antibody molecule described herein, or administering to the subject, an antibody molecule described herein; (optionally) (ii) contacting a reference sample (e.g., a control sample) with the antibody molecule, or administering to a reference subject (e.g., a control subject) the antibody molecule; and (iii) detecting formation of a complex between the antibody molecule and the anti-APRIL antibody in the sample or subject, or the reference sample or subject, wherein a change, e.g., a statistically significant change, in the formation of the complex in the sample or subject relative to the reference sample or subject is indicative of the presence of the anti-APRIL antibody in the sample or subject. The antibody molecule can be directly or indirectly labeled with a detectable substance to facilitate detection of the bound or unbound antibody molecule. Suitable detectable substances include various enzymes, prosthetic groups, fluorescent materials, luminescent materials and radioactive materials, as described above and described in more detail below.

The term "sample," as it refers to a sample used for detecting a polypeptide or a nucleic acid encoding the polypeptide, and includes, but is not limited to, body fluids (e.g., blood, serum, or urine), cells, cell lysates, proteins or membrane extracts of cells, or tissue samples (e.g., biopsies).

Complex formation between the antibody molecule and anti-APRIL antibody can be detected by measuring or visualizing either the antibody molecule bound to anti-APRIL antibody or unbound antibody molecule. Any suitable detection assays can be used, and conventional detection assays include an enzyme-linked immunosorbent assays (ELISA), a radioimmunoassay (RIA) or tissue immunohistochemistry. Alternative to labeling the antibody molecule, the presence of anti-APRIL antibody can be assayed in a sample by a competition immunoassay utilizing standards labeled with a detectable substance and an unlabeled antibody molecule. In this assay, the sample, the labeled standards and the antibody molecule are combined and the amount of labeled standard bound to the unlabeled binding molecule is determined. The amount of anti-APRIL antibody in the sample is inversely proportional to the amount of labeled standard bound to the antibody molecule.

The antibody molecules described herein can be used to diagnose disorders that can be treated or prevented by anti-APRIL antibody. The detection or diagnostic methods described herein can be used in combination with other methods described herein to treat or prevent a disorder described herein.

ENUMERATED EMBODIMENTS

1. An antibody molecule capable of binding to an anti-APRIL antibody, comprising: a heavy chain variable region (VH) comprising an HCDR1 amino acid sequence, an HCDR2 amino acid sequence, and an HCDR3 amino acid sequence of SEQ ID NO: 1; and a light chain variable region (VL) comprising an LCDR1 amino acid sequence, an LCDR2 amino acid sequence, and an LCDR3 amino acid sequence of SEQ ID NO: 2.
2. An antibody molecule capable of binding to an anti-APRIL antibody, comprising:

(a) a heavy chain variable region (VH) comprising 1, 2, or 3 of:

(i) an HCDR1 comprising the amino acid sequence of SEQ ID NO: 11, or an amino acid sequence having no more than 1, 2, or 3 amino acid differences therefrom, (ii) an HCDR2 comprising the amino acid sequence of SEQ ID NO: 12, or an amino acid sequence having no more than 1, 2, or 3 amino acid differences therefrom, and/or (iii) an HCDR3 comprising the amino acid sequence of SEQ ID NO: 13, or an amino acid sequence having no more than 1, 2, or 3 amino acid differences therefrom; and/or (b) a light chain variable region (VL) comprising 1, 2, or 3 of:

(iv) an LCDR1 comprising the amino acid sequence of SEQ ID NO: 14, or an amino acid sequence having no more than 1, 2, or 3 amino acid differences therefrom, (v) an LCDR2 comprising the amino acid sequence AAS, or an amino acid sequence having no more than 1, 2, or 3 amino acid differences therefrom, and/or (vi) an LCDR3 comprising the amino acid sequence of SEQ ID NO: 16, or an amino acid sequence having no more than 1, 2, or 3 amino acid differences therefrom.

3. The antibody molecule of embodiment 1 or 2, wherein the VH comprises the amino acid sequence of SEQ ID NO: 1, or an amino acid sequence having at least 85%, 90%, 95%, 96%, 97%, 98%, or 99% identity thereof, or differing by no more than 1, 2, 3, 4, 5, 6, 7, 8, 9, or 10 amino acids therefrom.

4. The antibody molecule of any of embodiments 1-3, wherein the VH comprises the amino acid sequence of SEQ ID NO: 1.

5. The antibody molecule of any of embodiments 1-4, wherein the VL comprises the amino acid sequence of SEQ ID NO: 2, or an amino acid sequence having at least 85%, 90%, 95%, 96%, 97%, 98%, or 99% identity thereof, or differing by no more than 1, 2, 3, 4, 5, 6, 7, 8, 9, or 10 amino acids therefrom.

6. The antibody molecule of any of embodiments 1-5, wherein the VL comprises the amino acid sequence of SEQ ID NO: 2.

7. The antibody molecule of any of embodiments 1-6, which comprises an antigen-binding fragment.

8 The antibody molecule of embodiment 7, wherein the antigen-binding fragment comprises a Fab, F(ab')2, Fv, scFv, or sc(Fv)2.

9. The antibody molecule of any of embodiments 1-8, which comprises a heavy chain constant region.

10. The antibody molecule of embodiment 9, wherein the heavy chain constant region comprises a heavy chain constant region of IgG1, IgG2, IgG3, or IgG4.

11. The antibody molecule of any of embodiments 1-10, which comprises a light chain constant region.

12. The antibody molecule of embodiment 11, wherein the light chain constant region comprises the light chain constant region of kappa or lambda light chain.

13. The antibody molecule of any of embodiments 1-12, which comprises an Fc region.

14. The antibody molecule of any of embodiments 1-13, which comprises a heavy chain comprising amino acids 18-458 of SEQ ID NO: 3 or amino acids 18-464 of SEQ ID NO: 4.

15. The antibody molecule of any of embodiments 1-14, which comprises a light chain comprising amino acids 18-235 of SEQ ID NO: 5.

16. The antibody molecule of any of embodiments 1-15, which comprises:

(a) a heavy chain comprising amino acids 18-458 of SEQ ID NO: 3 and a light chain comprising amino acids 18-235 of SEQ ID NO: 5; or (b) a heavy chain comprising amino acids 18-464 of SEQ ID NO: 4 and a light chain comprising amino acids 18-235 of SEQ ID NO: 5.

17. The antibody molecule of any of embodiments 1-16, which comprises a heavy chain comprising the amino acid sequence of SEQ ID NO: 3 or 4.

18. The antibody molecule of any of embodiments 1-17, which comprises a light chain comprising the amino acid sequence of SEQ ID NO: 5.

19. The antibody molecule of any of embodiments 1-18, which comprises:

(a) a heavy chain comprising the amino acid sequence of SEQ ID NO: 3 and a light chain comprising the amino acid sequence of SEQ ID NO: 5; or (b) a heavy chain comprising the amino acid sequence of SEQ ID NO: 4 and a light chain comprising the amino acid sequence of SEQ ID NO: 5.

20. The antibody molecule of any of embodiments 1-19, which is mAb 1H4. 21. The antibody molecule of any of embodiments 1-20, which is a mouse antibody molecule.

22. The antibody molecule of any of embodiments 1-21, which is an isolated antibody molecule.

23. The antibody molecule of any of embodiments 1-22, which is a monoclonal antibody molecule.

24. The antibody molecule of any of embodiments 1-23, which is an anti-idiotype antibody molecule.

25. The antibody molecule of any of embodiments 1-24, which binds to the VH, the VL, or both, of the anti-APRIL antibody.

26. The antibody molecule of any of embodiments 1-25, which binds to one or more (e.g., 2, 3, 4, 5 or 6) CDRs of the anti-APRIL antibody.

27. The antibody molecule of any of embodiments 1-26, which does not bind, or does not substantially bind, to the Fc region of the anti-APRIL antibody.

28. The antibody molecule of any of embodiments 1-27, which binds to the anti-APRIL antibody at an EC50 of less than 500 ng/mL, e.g., less than 400 ng/ml, 300 ng/ml, 200 ng/ml, 150 ng/mL, 120 ng/mL, 100 ng/mL, 90 ng/mL, 80 ng/mL, 70 ng/mL, 60 ng/mL, 50 ng/ml, 40 ng/ml, 35 ng/ml, 30 ng/mL, 25 ng/mL, 20 ng/ml, 15 ng/mL, 10 ng/ml, 5 ng/ml, 2 ng/mL, 1 ng/mL, or 0.1 ng/mL, e.g., 1 ng/ml to 150 ng/mL, 2 ng/mL to 100 ng/mL, 5 ng/ml to 50 ng/mL, or 10 ng/ml to 25 ng/ml, e.g., as determined by ELISA.

29. The antibody molecule of any of embodiments 1-28, which reduces (e.g., neutralizes, inhibits, or blocks) the binding of the anti-APRIL antibody to APRIL.

30. The antibody molecule of any of embodiments 1-29, which binds to anti-APRIL antibody that is not bound to APRIL.

31. The antibody molecule of any of embodiments 1-30, which does not bind, or does not substantially bind, to anti-APRIL antibody that is bound to APRIL.

32. The antibody molecule of any of embodiments 1-30, which binds to anti-APRIL antibody that is not bound to APRIL, and does not bind, or does not substantially bind, to anti-APRIL antibody that is bound to APRIL.

33. The antibody molecule of any of embodiments 1-32, which binds to anti-APRIL antibody that is not bound to APRIL, and does not bind, or does not substantially bind, to anti-APRIL antibody that is bound to APRIL.

34. The antibody molecule of any of embodiments 1-33, which bridges two anti-APRIL antibodies, e.g., binds to two anti-APRIL antibodies at the same time, e.g., as determined by a bridging ELISA assay.
35. The antibody molecule of any of embodiments 1-34, which competes for binding to APRIL with the anti-APRIL antibody.
36. The antibody molecule of any of embodiments 1-35, wherein the anti-APRIL antibody binds to human APRIL.
37. The antibody molecule of any of embodiments 1-36, wherein the anti-APRIL antibody is sibeprenlimab.
38. An antibody molecule that competes for binding to an anti-APRIL antibody with an antibody molecule of any of embodiments 1-37.
39. An antibody molecule that binds to the same or overlapping epitope as the epitope recognized by an antibody molecule of any of embodiments 1-37.
40. A method of detecting an anti-APRIL antibody, comprising:
(a) contacting an antibody molecule of any of embodiments 1-39 with a sample; and
(b) determining the formation of a complex between the antibody molecule and the sample (e.g., between the antibody molecule and the anti-APRIL antibody in the sample), thereby detecting the anti-APRIL antibody.
41. A method of evaluating a sample, comprising:
(a) contacting an antibody molecule of any of embodiments 1-39 with the sample; and
(b) determining the formation of a complex between the antibody molecule and the sample (e.g., between the antibody molecule and the anti-APRIL antibody in the sample), thereby evaluating the sample.
42. The method of embodiment 40 or 41, further comprising:
(c) contacting the antibody molecule with a reference sample; and
(d) determining the formation of a complex between the antibody molecule and the reference sample (e.g., between the antibody molecule and the anti-APRIL antibody in the reference sample).
43. The method of any of embodiments 40-42, further comprising providing a sample or reference sample before the antibody molecule is contacted with the sample or reference sample.
44. The method of any of embodiments 40-43, which is an ELISA assay.
45. The method of any of embodiments 40-44, which is an anti-drug assay, a toxicology assay, or a GxP assay.
46. A method of detecting an anti-APRIL antibody, comprising:
(a) administering an antibody molecule of any of embodiments 1-39 to a subject; and
(b) determining the formation of a complex between the antibody molecule and the subject (e.g., between the antibody molecule and the anti-APRIL antibody in the subject), thereby detecting the anti-APRIL antibody.
47. A method of evaluating a subject, comprising:
(a) administering an antibody molecule of any of embodiments 1-39 to the subject; and
(b) determining the formation of a complex between the antibody molecule and the subject (e.g., between the antibody molecule and an anti-APRIL antibody in the subject), thereby evaluating the subject.
48. A composition (e.g., a pharmaceutical composition) comprising an antibody molecule of any of embodiments 1-39, optionally wherein the composition comprises a pharmaceutically acceptable carrier, excipient or stabilizer.
49. A nucleic acid (e.g., an isolated nucleic acid) encoding the VH, VL, or both, of an antibody molecule of any of embodiments 1-39.
50. The nucleic acid of embodiment 49, which comprises nucleotides 52-1374 of SEQ ID NO: 8, or a nucleotide sequence having at least 85%, 90%, 95%, 96%, 97%, 98%, or 99% identity thereto, or differing by no more than 1, 5, 10, 15, 20, 25, 30, 35, 40, 45, or 50 nucleotides therefrom.
51. The nucleic acid of embodiment 49 or 50, which comprises nucleotide sequence of SEQ ID NO: 8.
52. The nucleic acid of embodiment 49, which comprises nucleotides 52-1392 of SEQ ID NO: 9, or a nucleotide sequence having at least 85%, 90%, 95%, 96%, 97%, 98%, or 99% identity thereto, or differing by no more than 1, 5, 10, 15, 20, 25, 30, 35, 40, 45, or 50 nucleotides therefrom.
53. The nucleic acid of embodiment 49 or 52, which comprises the nucleotide sequence of SEQ ID NO: 9.
54. The nucleic acid of any of embodiments 49-53, which comprises nucleotides 52-705 of SEQ ID NO: 10, or a nucleotide sequence having at least 85%, 90%, 95%, 96%, 97%, 98%, or 99% identity thereto, or differing by no more than 1, 5, 10, 15, 20, 25, 30, 35, 40, 45, or 50 nucleotides therefrom.
55. The nucleic acid of any of embodiments 49-54, which comprises the nucleotide sequence of SEQ ID NO: 10.
56. A vector (e.g., an expression vector) comprising a nucleic acid of any of embodiments 49-55.
57. The vector of embodiment 56, wherein the vector comprises a promoter operably linked to the nucleic acid.
58. A cell (e.g., a host cell) comprising a nucleic acid of any of embodiments 49-55 or a vector of embodiment 56 or 57.
59. A method of producing an antibody molecule, comprising culturing the cell of embodiment 58 under conditions suitable for gene expression.
60. The method of embodiment 59, which further comprises isolating or purifying the antibody molecule.
61. The method of embodiment 59 or 60, wherein the antibody molecule is produced at a concentration of 0.2 mg/mL to 5 mg/mL, e.g., 0.5 mg/mL to 1.5 mg/mL.

EXAMPLES

Example 1: Generation of Anti-Idiotype Antibody

Mice were immunized with sibeprenlimab. To assess specificity in the pre-subclone screen, sibeprenlimab was used as a counter-screen reagent.

The first round of immunizations was successful in eliciting a strong serologic response to sibeprenlimab shown in the titer test and all three mice were harvested for fusion. For the titer test, sibeprenlimab was coated on ELISA plates and anti-sera was titrated down the plate from each of the three mice with a normal mouse serum control. All three mice demonstrated immune-sensitization to sibeprenlimab compared to normal mouse serum and were recommended and used for hybridoma generation.

Lymph nodes harvested from three mice yielded eight 96-well plates of hybridomas after fusion. Hybridomas were plated based on cell density to maximize monoclonality. The primary screen of eight fusion plates assessed sibeprenlimab binding by enzyme linked immunosorbent assay (ELISA) and counter screened against reactivity to human IgG2. The clones positive for sibeprenlimab (and negative for human IgG2) were ranked, selected, and transferred to a new single 96-well plate composed of 75 clones and 20 blank wells and one well containing an anti-sera positive control. Clones were expanded in a new 96-well plate for the pre-subclone screen, and supernatants were used in a secondary screen for binding to sibeprenlimab, human IgG2, human IgG, 20% pooled human sera, 20% pooled cynomolgus sera, and 0.8% BSA. Of the 75 clones, 68 clones showed reactivity to sibeprenlimab and little to no reactivity to the human IgG2 counter screen, human IgG, 20% pooled human sera, 20% pooled cynomolgus sera, and 0.8% BSA. The 7 clones that showed binding to human IgG2 and/or human Ig were eliminated from all further analysis. Most clones showed a maximum signal of an OD value ≥1.5 at 450 nM. 68 parental clones were frozen, and supernatants were sent for tertiary screening.

Clone Selection

In an Octect assay, all 68 hybridoma clones were titered with anti-mouse IgG Fv biosensor tips on the Octet and normalized to 1 μg/mL in 1×PBS and stored at 4° C. to use in tertiary screening assays. The 68 candidate anti-ID hybridomas were screened for binding to a panel of mAbs to examine specificity of the anti-ID. The mAbs from the panel were coated on ELISA plates and incubated at 4° C. overnight prior to running each specificity ELISA. Based on the results of the specificity screen, 24 hybridomas demonstrated high reactivity to sibeprenlimab, mAb 2419 (chimeric hIgG1), and mAb 2419-043 (IgG2, similar to sibeprenlimab); and low/no reactivity to control mAbs. The mAb 2419 is the murine IgG1 version of the humanized sibeprenlimab; the CDR loops are conserved but the framework regions have alterations, and the constant regions are different. Binding to mAb 2419 is consistent with the anti-ID targeting the CDR region of sibeprenlimab.

Figure 1A:
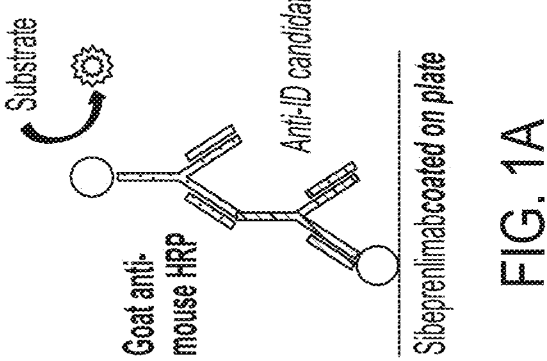

The top 24 hybridomas were further characterized in the binding ('PK-like') and bridging ELISA (FIGS. 1A-1B). For purposes of the bridging ELISA assay, sibeprenlimab was biotinylated. In the assay, the biotinylated version of sibeprenlimab was detectable by both goat anti-human IgG and streptavidin HRP secondary antibodies however the non-biotinylated sibeprenlimab was only detected by the goat anti-human IgG, as expected.

Based on the data from the binding and bridging ELISAs, all 24 selected clones showed strong binding to sibeprenlimab with varied $EC_{50}$ values. Of the 24 clones, 7 were identified as 'bridgers' at varying degrees. The list of clones to pursue further characterization was based on the ability of the mouse mAb to form a bridge in the bridging ELISA. The hybridoma clones bound sibeprenlimab well in an indirect binding ELISA, but only a subset performed well in the bridging ELISA. All clones were also tested to determine mAb isotype. Clones with an IgG2 isotype and favorable binding/bridging profiles were initially chosen for the subcloning, due to the ease and reproducibility of purification on a Protein A column in the scale-up of producing the anti-idiotype. Table 1 summarizes the 10 clones were chosen for subcloning and the summary of results to this initial panel of experiments.

TABLE 1

Subclone selection summary

| Clone Name | EC50 | Expression Rate of Hybridoma (μg/mL) |
|---|---|---|
| 1B8 | 106.2 | 60 |
| 1H4 | 20.10 | 54.9 |
| 6A3 | 9.567 | 30.9 |
| 1E5 | 12.71 | 23.5 |
| 6C1 | 36.99 | 39 |
| 3F4 | 12.10 | 33.5 |
| 1A5 | 8.194 | 49.2 |
| 6C12 | 10.66 | 22.4 |
| 2F5 | 22.18 | 23.0 |
| 6H5 | 6.399 | 60 |

Final Subclone Characterization

The ten subcloned hybridomas (2 parentals each) were prepared as (1) frozen hybridomas, (2) hybridoma supernatants, and (3) live cells in 6-well plates. The subclone supernatants were titered with anti-mouse IgG Fv biosensor tips on the Octet, and normalized to 1 μg/mL in 1×PBS and stored at 4° C. for use in later experiments. The 6-well plates of live hybridoma cells were passaged using standard hybridoma techniques. *Hybridoma* cells were frozen down within the first weeks of passaging.

Hybridomas were maintained at 65-85% plate confluency or at a concentration between 0.25 and $1.0\times10^6$ cells/mL. General passaging was performed at a 1:5 or 1:10 scaling every 48-72 hours.

The hybridoma supernatants were characterized using the panel of tertiary screening assays in order to determine the final subclones to pursue for purification and subsequent characterization. Experiments to characterize the 20 subclones included the sibeprenlimab binding ELISA, the bridging ELISA, and the rapid ELISA mAb isotyping. Upon completion of this round of experiments, some subclones at 1 μg/mL had a reduced affinity to sibeprenlimab in the binding ELISA and were eliminated from selection. Based on results from the bridging ELISA, 5 of the 20 subclones were still strong 'bridgers'; 7 of the 10 selected clones were strong 'bridgers' prior to subcloning. Upon testing the isotypes of the subclones, no IgG2a/b isotype was observed (prior to subcloning, 3 of the 10 parentals were identified as IgG2s). Changes in the properties of the subclones meant there were no IgG2a/b hybridomas for the simple protein A purification strategy. Therefore, efforts were focused on (1) purification of hybridoma using protein G and low IgG FBS and (2) sequencing and cloning variable regions of lead hybridomas into a mouse IgG2 vector. Table 2 summarizes the characterization of all 20 subclones. 1A5.F4, 1H4.F4, and 6A3.E6 were chosen for large-scale hybridoma scale up.

TABLE 2

Subclones Sequencing/Cloning Selection Summary

| Subclone | Sibeprenlimab | Bridging Capacity | Isotype* | Expression Rate of Supernatant (μg/ml) |
|---|---|---|---|---|
| 1A5.F4 | +++ | ++ | IgG1/IgG3 κ | 61.6 |
| 1A5.F6 | +++ | ++ | IgG1 κ | 68.1 |
| 1B8.F4 | + | − | IgG1 κ | 43.2 |
| 1B8.G3 | +++ | − | IgG1/IgG2b κ | 51.4 |
| 1E5.E4 | +++ | − | Undetermined | 23.1 |
| 1E5.G3 | +++ | − | IgG1 κ | 22.6 |
| 1H4.F4 | +++ | +++ | IgG1 κ | 40.8 |
| 1H4.G3 | +++ | − | IgG1/IgG2a κ | 47.5 |

TABLE 2-continued

Subclones Sequencing/Cloning Selection Summary

| Subclone | Sibeprenlimab | Bridging Capacity | Isotype* | Expression Rate of Supernatant (μg/ml) |
|---|---|---|---|---|
| 2F5.C11 | +++ | − | IgG1 κ | 24.7 |
| 2F5.D10 | +++ | − | IgG1 κ | 26.1 |
| 3F4.B11 | +++ | − | IgG1 κ | 48.9 |
| 3F4.F4 | +++ | − | IgG1 κ | 71.5 |
| 6A3.E6 | +++ | +++ | IgG1 κ | 75.8 |
| 6A3.F8 | +++ | +++ | IgG1 κ | 57.5 |
| 6C1.C7 | ++ | − | IgG1 κ | 64.4 |
| 6C1.C8 | +++ | + | IgG1/IgG2b κ | 58.1 |
| 6C12.F7 | +++ | + | IgG1 κ | 45.7 |
| 6C12.F12 | +++ | + | IgG1 κ | 54.1 |
| 6H5.D6 | +++ | − | IgG1 λ | 16.9 |
| 6H5.D7 | +++ | + | IgG1 κ | 55.6 |

+++ Maximal Signal; OD Value of 1.5 or higher
++ OD Value ≥ 1.0
+ OD Value between 0.4 and 0.99
− Minimal Signal; OD Value < 0.2
*Isotype determination is not exact Sequence and Recombinant Expression 1A5.F4, 1A5.F6, 1H4.F4, 6A3.E6, 6A3.F8, and 6C12.F12 were chosen to culture in a 6-well plate and move forward to sequence and clone into a mouse IgG2a platform vector. Four unique productive HC and LC sequences were identified. The binding and bridging ELISA was run using supernatants from all 4 transfections. 1A5 and both 1H4 (HC_VH1 and HC_VH4_5_10) transfections did not retain sibeprenlimab binding or bridging. Some activity was retained for 6C12. 6C12 was therefore purified using a Protein A column and re-tested for activity. Compared to the 6C12 hybridoma supernatant, recombinant purified 6C12 had lower bridging activity and slightly lower binding activity-which was not ideal for the final anti-idiotype antibody. The effort to produce the anti-idiotype recombinantly was re-visited with the final candidate, 1H4.

The three subclones 1A5.F4, 1H4.F4, and 6A3.E6 were chosen based on activity in the established panel of experiments to pursue large-scale hybridoma production and purification, followed by qualification.

Scale-Up of Hybridomas in CeLLine Bioreactor Flasks

Figures 2A, 2B:
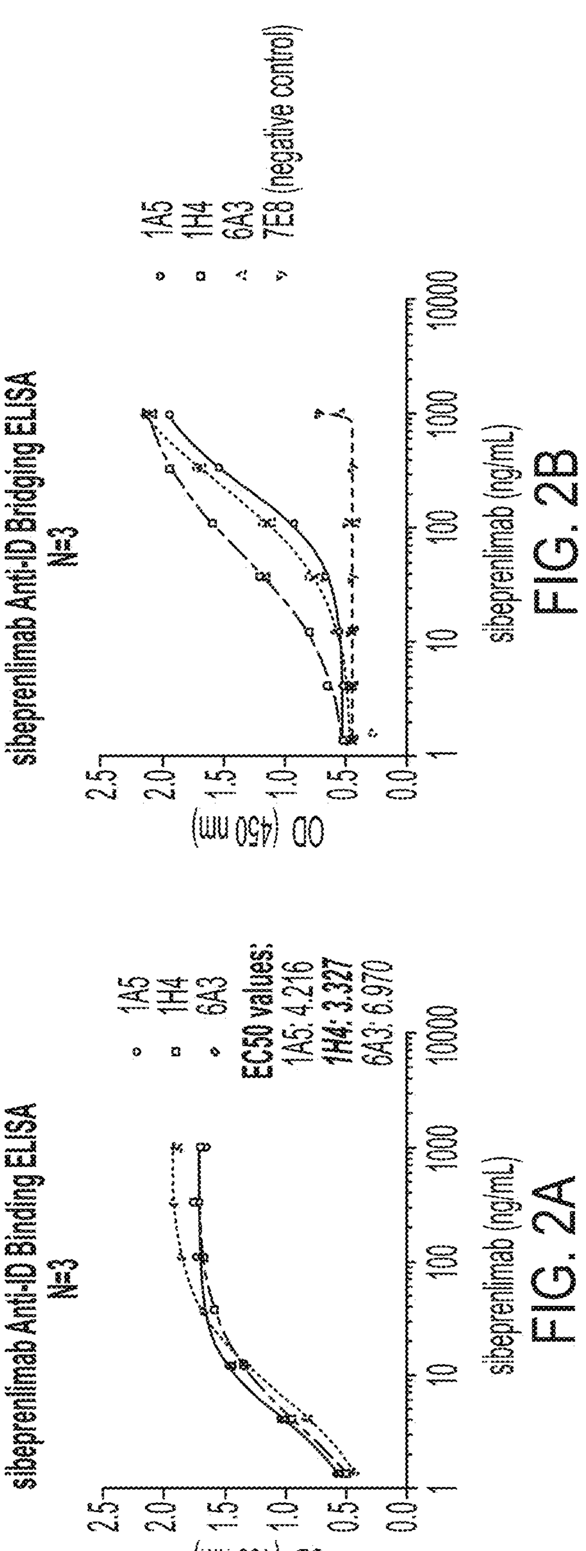
FIGS. 2A-2C depicts the characterization of anti-ID candidates (small scale purifications). The results of sibeprenlimab anti-ID binding ELISA (FIG. 2A), sibeprenlimab anti-ID bridging ELISA (FIG. 2B), and 2419 chimeric IgG1 binding ELISA (FIG. 2C) are shown.
Figure 2C:
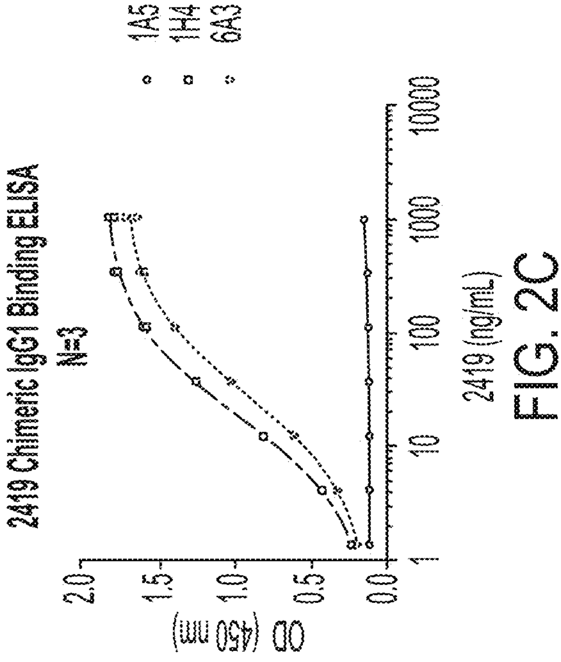

1A5.F4, 1H4.F4, and 6A3.E6 were scaled up to 5 T-150 flasks in low IgG media. Once confluent, one of the T-150 flasks for each subclone was used to seed a CeLLine 1000 Bioreactor Flask, incubated at 37° C. and 5% $CO_2$ for 7 days before harvest 1. The other 4 T-150 flasks were incubated at 37° C. and 5% $CO_2$ for 7 days, pooled, harvested, and purified on a 1 mL Protein G column, dialyzed in 1×PBS, sterile filtered, and quantified. In FIGS. 2A-2C, the small-scale purification lots of 1A4, 1H4, and 6A3 were characterized by binding ELISA (FIG. 2A), bridging ELISA (FIG. 2B), and specificity ELISA (FIG. 2C) to 2419 before choosing the anti-ID to purify from its respective CeLLine 1000 Bioreactor Flask. This parallel workflow of small-scale purification characterizations during incubation/production in the CeLLine 1000 Bioreactor flasks allowed for faster large-scale production of the selected anti-ID, as production in the Bioreactor flask can take up to 4 weeks.

Figure 3B:
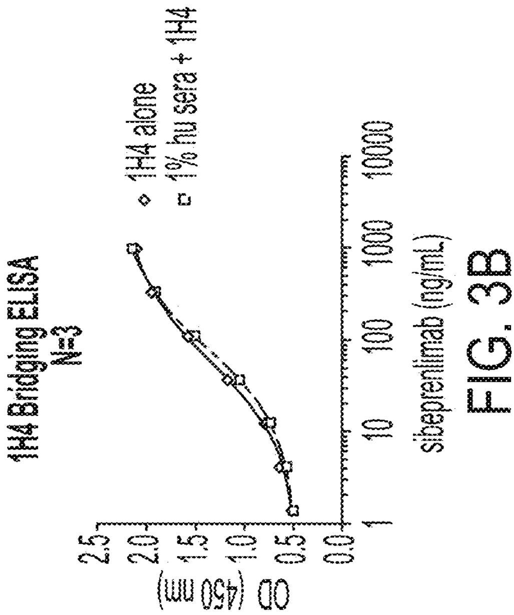
FIGS. 3A-3C depicts the results of bridging ELISA in the presence of 1% human sera (small scale purification). Subclones 1A5 (FIG. 3A), 1H4 (FIG. 3B) and 6A3 (FIG. 3C) were tested.
Figure 3A:
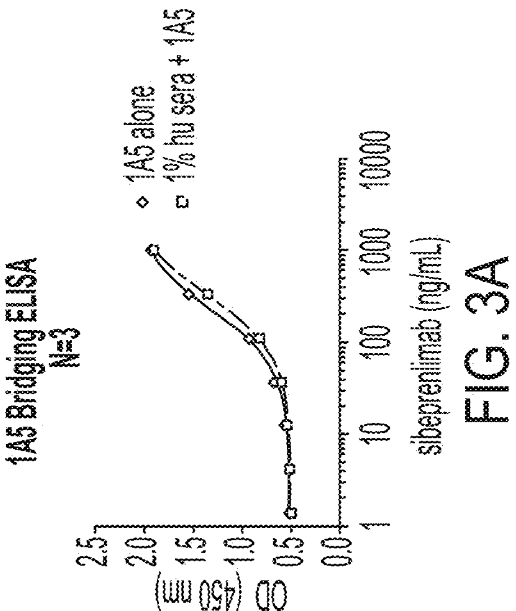
Figure 3C:
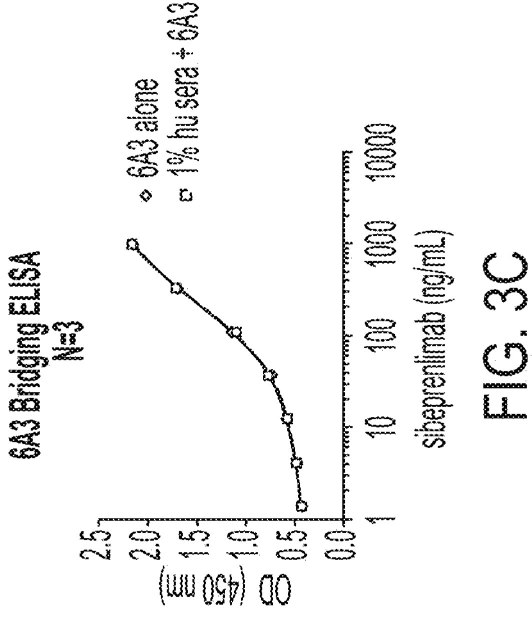

The binding data in FIGS. 2A-2C suggest all three anti-ID candidates bind sibeprenlimab similarly. 1H4 appears to be the strongest 'bridger', and only 1H4 and 6A3 bind to 2419; 2419 has the same CDR regions as sibeprenlimab. In FIGS. 3A-3C, the bridging ELISA was also performed in the presence of 1% human sera (in assay) to ensure no cross-reactivity. Additionally, SDS PAGER was run for 1A5, 1H4, and 6A3 to confirm no mixtures in heavy chain and light chain. Reduced and non-reduced samples were run on a 4-12% Bis-Tris gel and bands were visualized with Simple Blue Strain. The profile of 1A5 (reduced) slightly differs from that of 1H4 and 6A3.

Production for GXP Assays

Figure 4A:
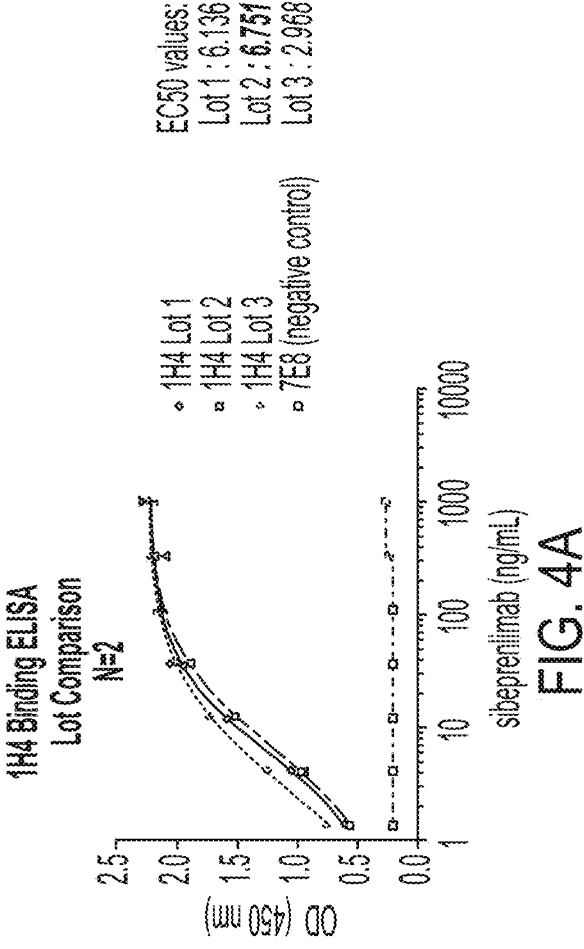
FIGS. 4A-4C depicts the characterization of 1H4 by binding ELISA (freeze/thaw stability). The results of 1H4 binding ELISA lot comparison (FIG. 4A), 1H4 Lot #2 stability binding ELISA (FIG. 4B), and 1H4 Lot #3 stability binding ELISA (FIG. 4C) are shown.
Figures 4B, 4C:
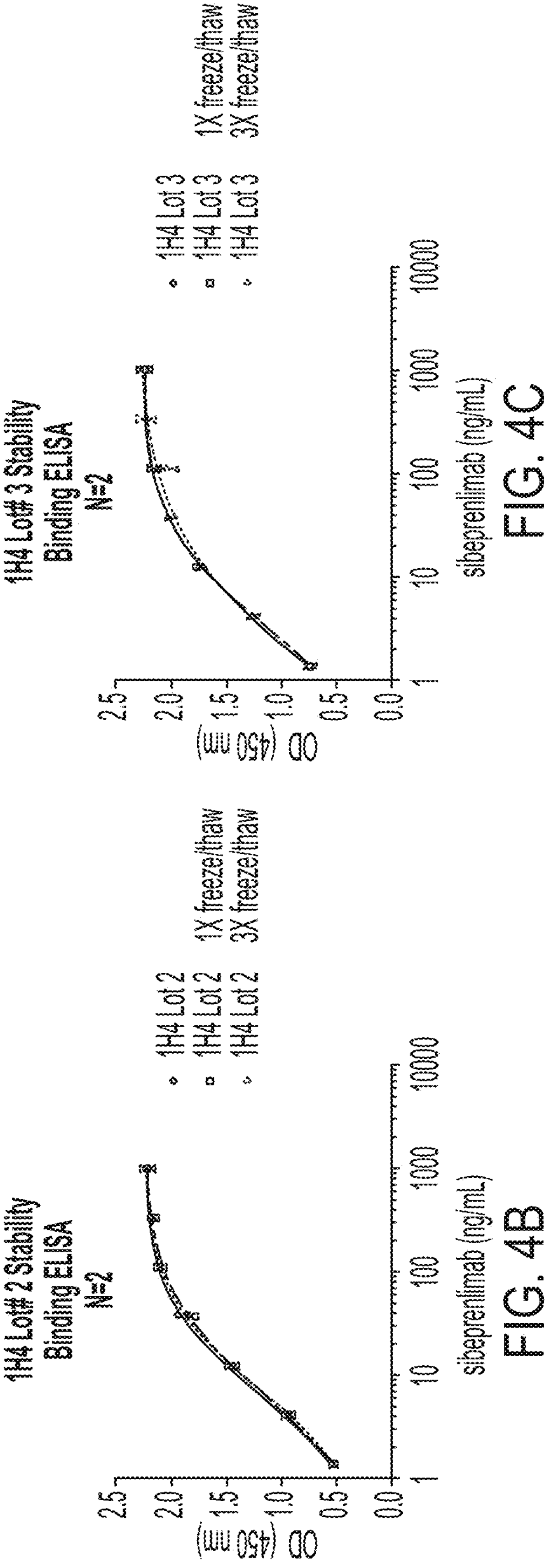
Figures 5A, 5B:
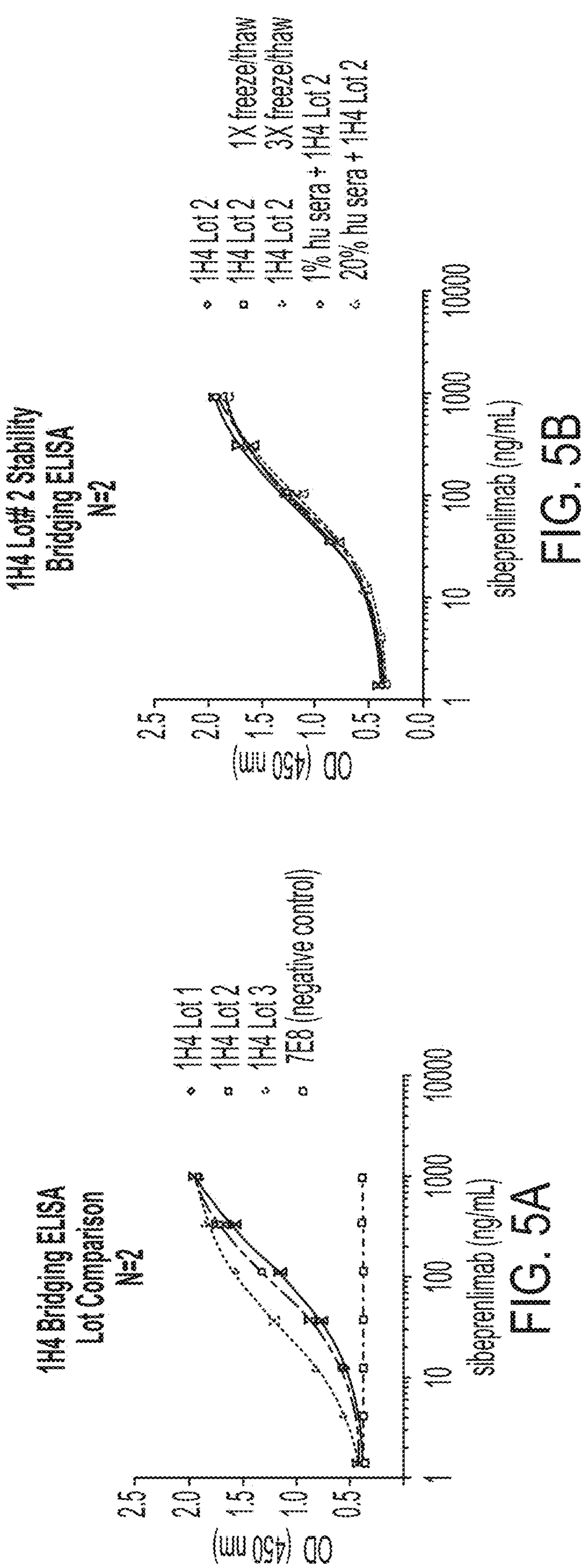
FIGS. 5A-5C depicts the characterization of 1H4 by bridging ELISA (freeze/thaw stability and in the presence of 1% and 20% human serum). The results of 1H4 bridging ELISA lot comparison (FIG. 5A), 1H4 Lot #2 stability bridging ELISA (FIG. 5B), and 1H4 Lot #3 stability bridging ELISA (FIG. 5C) are shown.
Figure 5C:
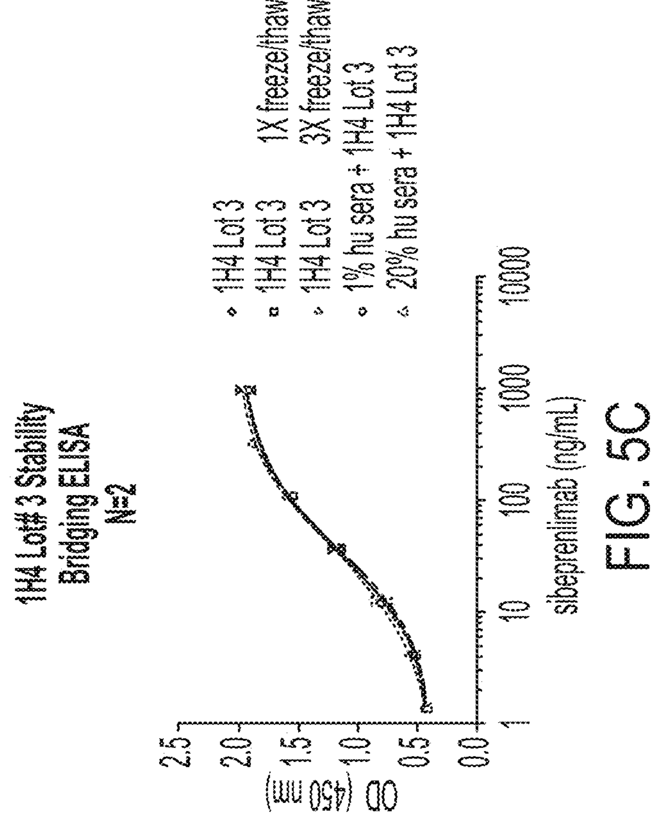

Based on the characterization data, 1H4 was chosen as the anti-ID mAb to produce for GXP assays. The IgG1 hybridoma, produced in the CeLLine 1000 Bioreactor Flask, was purified on a 1 mL Protein G column. Three hybridoma produced lots of 1H4 were qualified for GXP assays by performing 1× and 3× freeze/thaws and assessing by binding ELISA (FIGS. 4A-4C), bridging ELISA (in the presence of 1% and 20% human sera, to ensure no cross reactivity) (FIGS. 5A-5C), reduced and non-reduced SDS-PAGE (4-12% Bis-Tris gel and visualized with Simple Blue Stain), and mAb Isotyping ELISA to confirm IgG1 K isotype.

These lots of 1H4 were determined to behave similarly in binding/bridging ELISAs. 1H4 in the presence of 1% and 20% human sera and one and three times freeze/thaw had no effect on SDS-PAGE reduced and non-reduced profiles and on performance in binding/bridging ELISAs.

Additional lots of hybridoma produced 1H4 were similarly characterized using the binding and bridging ELISA methods and SDS-PAGE (reduced and non-reduced, 4-12% Bis-Tris gel and visualized with Simple Blue Stain) and compared to previous lots. The additional lots of 1H4 demonstrated binding and bridging activity comparable to previous lots. Additionally, the SDS-PAGE reduced and non-reduced profiles were comparable.

Sequence and Recombinant Expression of 1H4

1H4 was for ADA Assay Development. The sequence of the 1H4.F4 anti-idiotype was identified for recombinant expression in expi293 cells.

In order to compare activity of 1H4 in an IgG1 versus an IgG2 backbone, both were pursued. The 1H4_VH sequence and IgG1 constant region were cloned into a vector. The 1H4_Vk sequence was also clone into a vector. The nucleotide sequences were humanized and codon-optimized. Colonies were sequenced and plasmids were maxiprepped using standard laboratory methods. Two 200 mL expi293 transfections were set up with 1H4 (IgG1) and 1H4 (IgG2). The IgG1 was purified on a 1 mL Protein G column, and the IgG2 was purified on a 1 mL Protein A column. It is notable that the IgG1 recombinant was expressed at lower levels compared to the IgG2 recombinant.

Figures 6A, 6B:
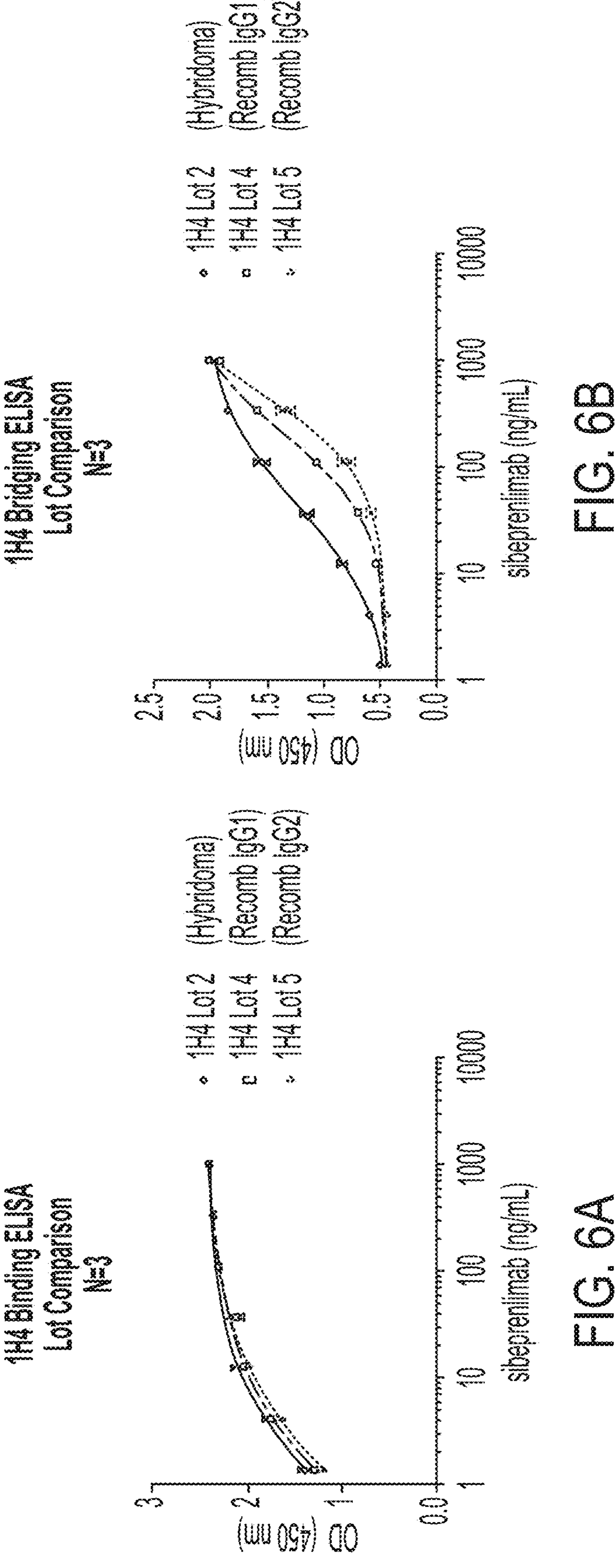
FIGS. 6A-6B depicts the hybridoma 1H4 vs. recombinant 1H4 binding (FIG. 6A) and bridging (FIG. 6B) results.

The hybridoma produced 1H4 was compared to the recombinantly produced and purified 1H4 (IgG1 backbone and IgG2 backbone) in FIGS. 6A-6B. The three lots looked comparable in the binding ELISA, however bridging results indicate the 1H4 hybridoma is the best 'bridger' with some variability between the recombinant lots. Additionally, the hybridoma produced 1H4 was compared to the recombinantly produced and purified 1H4 (IgG1 backbone and IgG2 backbone) in SDS-PAGE (4-12% Bis-Tris gel and visualized with Simple Blue Stain). The hybridoma produced 1H4 and recombinantly produced 1H4 had comparable reduced and non-reduced SDS-PAGE profiles.

Binding "Free" Vs. "Total" Sibeprenlimab

Figure 7:
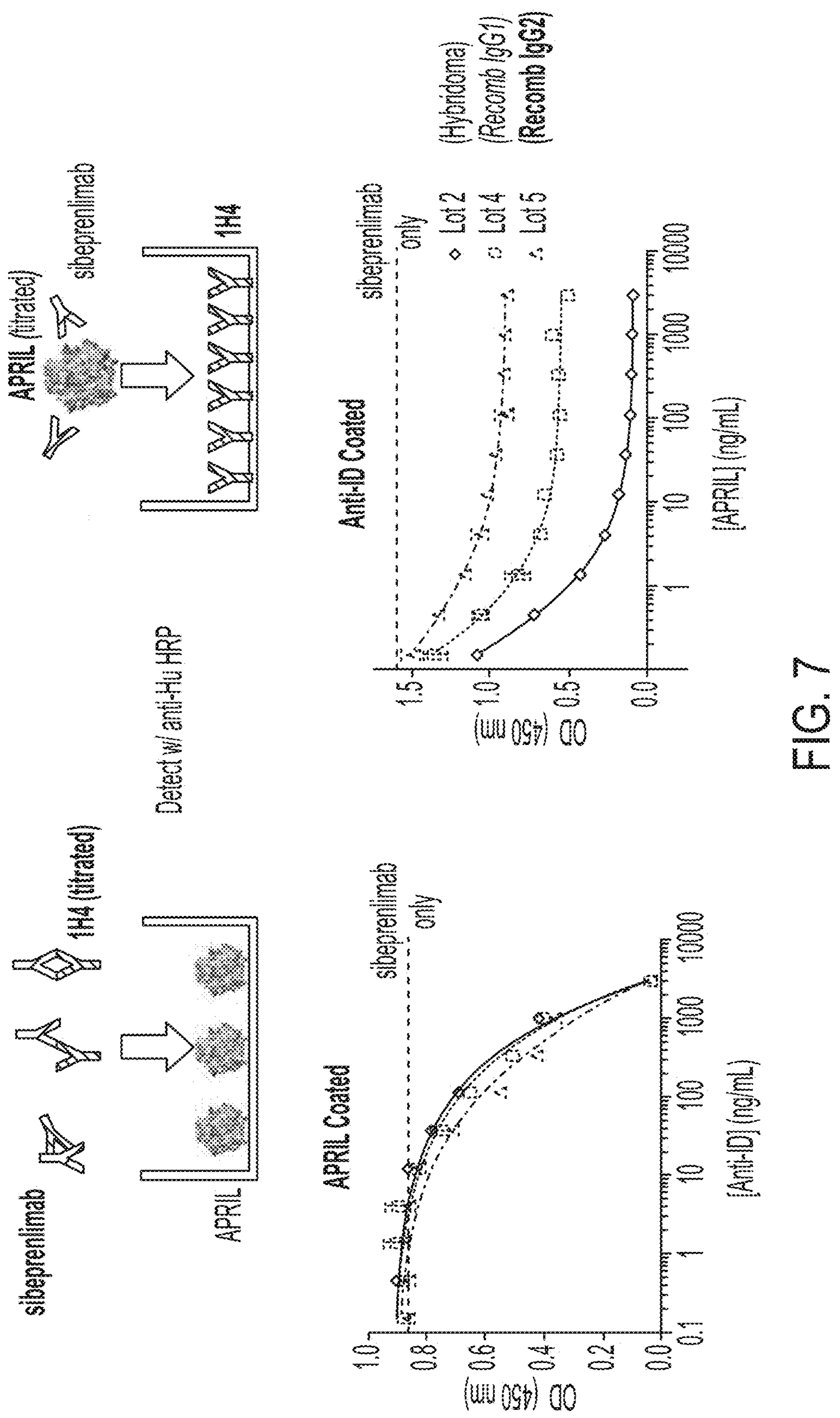
FIG. 7 depicts the results of sibeprenlimab anti-idiotype (1H4) specificity ELISA.

To further characterize the sibeprenlimab anti-idiotype antibody 1H4, 1H4 was evaluated for binding specificity whether it recognized "free drug" (i.e., sibeprenlimab unbound to APRIL) or "total drug" (i.e., sibeprenlimab bound or unbound to APRIL). Sibeprenlimab at 12 ng/ml and titrated 1H4 were pre-incubated overnight at 4° C. and added to a pre-coated APRIL plate (0.5 μg/mL). Similarly, Sibeprenlimab at 12 ng/mL and titrated APRIL were pre-incubated overnight at 4° C. and added to a pre-coated 1H4 plate (1.0 μg/mL). In FIG. 7, 1H4 was found to be neutralizing (i.e., blocked sibeprenlimab binding to APRIL), and only recognized "free drug" and not "total drug" i.e., sibeprenlimab in the context bound to APRIL.

SUMMARY

Anti-idiotype (anti-ID) monoclonal antibodies that recognize sibeprenlimab were generated. 1A5, 1H4, and 6A3 were characterized, and 1H4 was determined suitable for use in preclinical and clinical antibody drug development assays. Production of 1H4 was performed using the hybridoma cell line in a CeLLine 1000 Bioreactor Flask. 1H4 was later sequenced and recombinantly expressed and was produced in both an IgG1 and IgG2 VH backbone and evaluated in the panel of anti-ID characterization assays.

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. An antibody molecule capable of binding to an anti-APRIL antibody, comprising:
- (a) a heavy chain variable region (VH) comprising
  - (i) an HCDR1 comprising the amino acid sequence of SEQ ID NO: 11,
  - (ii) an HCDR2 comprising the amino acid sequence of SEQ ID NO: 12, and
  - (iii) an HCDR3 comprising the amino acid sequence of SEQ ID NO: 13; and
- (b) a light chain variable region (VL) comprising
  - (iv) an LCDR1 comprising the amino acid sequence of SEQ ID NO: 14,
  - (v) an LCDR2 comprising the amino acid sequence AAS, and
  - (vi) an LCDR3 comprising the amino acid sequence of SEQ ID NO: 16.

2. The antibody molecule of claim 1, wherein the VH comprises the amino acid sequence of SEQ ID NO: 1, or an amino acid sequence having at least 85%, 90%, 95%, 96%, 97%, 98%, or 99% identity thereof, or differing by no more than 1, 2, 3, 4, 5, 6, 7, 8, 9, or 10 amino acids therefrom; and/or
- wherein the VL comprises the amino acid sequence of SEQ ID NO: 2, or an amino acid sequence having at least 85%, 90%, 95%, 96%, 97%, 98%, or 99% identity thereof, or differing by no more than 1, 2, 3, 4, 5, 6, 7, 8, 9, or 10 amino acids therefrom.

3. The antibody molecule of claim 1, which comprises an antigen-binding fragment.

4. The antibody molecule of claim 3, wherein the antigen-binding fragment comprises a Fab, F(ab')2, Fv, scFv, or sc(Fv)2.

5. The antibody molecule of claim 1, which comprises a heavy chain constant region and/or a light chain constant region.

6. The antibody molecule of claim 5, wherein the heavy chain constant region comprises a heavy chain constant region of IgG1, IgG2, IgG3, or IgG4.

7. The antibody molecule of claim 5, wherein the light chain constant region comprises the light chain constant region of kappa or lambda light chain.

8. The antibody molecule of claim 1, which comprises an Fc region.

9. The antibody molecule of claim 1, which comprises:

(a) a heavy chain comprising amino acids 18-458 of SEQ ID NO: 3 and a light chain comprising amino acids 18-235 of SEQ ID NO: 5; and/or (b) a heavy chain comprising amino acids 18-464 of SEQ ID NO: 4 and a light chain comprising amino acids 18-235 of SEQ ID NO: 5.

10. The antibody molecule of claim 1, which comprises:

(a) a heavy chain comprising the amino acid sequence of SEQ ID NO: 3 and a light chain comprising the amino acid sequence of SEQ ID NO: 5; and/or (b) a heavy chain comprising the amino acid sequence of SEQ ID NO: 4 and a light chain comprising the amino acid sequence of SEQ ID NO: 5.

11. The antibody molecule of claim 1, which is a mouse antibody molecule, an isolated antibody molecule, a monoclonal antibody molecule, or an anti-idiotype antibody molecule.

12. The antibody molecule of claim 1, which:

(a) binds to the VH, the VL, or both, of the anti-APRIL antibody;

(b) binds to one or more CDRs of the anti-APRIL antibody;

(c) does not bind, or does not substantially bind, to the Fc region of the anti-APRIL antibody; and/or (d) binds to the anti-APRIL antibody at an EC50 of less than 500 ng/ml.

13. The antibody molecule of claim 1, which:

(a) reduces the binding of the anti-APRIL antibody to APRIL;

(b) binds to anti-APRIL antibody that is not bound to APRIL;

(c) does not bind, or does not substantially bind, to anti-APRIL antibody that is bound to APRIL;

(d) bridges two anti-APRIL antibodies; and/or (e) competes for binding to APRIL with the anti-APRIL antibody.

14. The antibody molecule of claim 1, wherein the anti-APRIL antibody binds to human APRIL or is sibeprenlimab.

15. A method of detecting an anti-APRIL antibody, comprising:

(a) contacting the antibody molecule of claim 1 with a sample; and (b) determining the formation of a complex between the antibody molecule and the anti-APRIL antibody in the sample, thereby detecting the anti-APRIL antibody.

16. A method of evaluating a sample, comprising:

(a) contacting the antibody molecule of claim 1 with the sample; and (b) determining the formation of a complex between the antibody molecule and the anti-APRIL antibody in the sample, thereby evaluating the sample.

17. A method of detecting an anti-APRIL antibody, comprising:

(a) administering the antibody molecule of claim 1 to a subject; and (b) determining the formation of a complex between the antibody molecule and the anti-APRIL antibody in the subject, thereby detecting the anti-APRIL antibody.

18. A method of evaluating a subject, comprising:

(a) administering the antibody molecule of claim 1 to the subject; and (b) determining the formation of a complex between the antibody molecule and an anti-APRIL antibody in the subject, thereby evaluating the subject.

19. A composition comprising the antibody molecule of claim 1.

20. One or more nucleic acids encoding the VH and VL of the antibody molecule of claim 1.

21. A vector comprising the one or more nucleic acids of claim 20.

22. A cell comprising the one or more nucleic acids of claim 20.

23. A method of producing an antibody molecule, comprising culturing the cell of claim 22 under conditions suitable for gene expression.

* * * * *

SEQUENCE LISTING

```
Sequence total quantity: 22
SEQ ID NO: 1            moltype = AA  length = 117
FEATURE                 Location/Qualifiers
source                  1..117
                        mol_type = protein
                        organism = synthetic construct
SEQUENCE: 1
EVRLLQSGGG LVQPGGSLKL SCAASGIDFS RYWMSWVRRA PGQGLEWIGE INPDSSTINY  60
APSLKDKFII SRDNAKKTLY LQMSKVRSED KVFYYCAIYY DYAMDFWGQG TSVTVSS     117

SEQ ID NO: 2            moltype = AA  length = 113
FEATURE                 Location/Qualifiers
source                  1..113
                        mol_type = protein
                        organism = synthetic construct
SEQUENCE: 2
DIVLTQSPAS LAVSLGQRAT ISCRASESVD NYGISFMNWF QQKPGQPPKL LIYAASNQGS  60
GVPARFSGSG SGTDFSLNIH PMEEDDTAMY FCQQNKEVPY TFGGGTKVEI KRT         113

SEQ ID NO: 3            moltype = AA  length = 458
FEATURE                 Location/Qualifiers
source                  1..458
                        mol_type = protein
                        organism = synthetic construct
SEQUENCE: 3
MRAWIFFLLC LAGRALAEVR LLQSGGGLVQ PGGSLKLSCA ASGIDFSRYW MSWVRRAPGQ  60
GLEWIGEINP DSSTINYAPS LKDKFIISRD NAKKTLYLQM SKVRSEDKVF YYCAIYYDYA  120
MDFWGQGTSV TVSSAKTTPP SVYPLAPGSA AQTNSMVTLG CLVKGYFPEP VTVTWNSGSL  180
SSGVHTFPAV LQSDLYTLSS SVTVPSSTWP SETVTCNVAH PASSTKVDKK IVPRDCGCKP  240
CICTVPEVSS VFIFPPKPKD VLTITLTPKV TCVVVDISKD DPEVQFSWFV DDVEVHTAQT  300
QPREEQFNST FRSVSELPIM HQDWPNGKEF KCRVNSAAFP APIEKTISKT KGRPKAPQVY  360
TIPPPKEQMA KDKVSLTCMI TDFFPEDITV EWQWNGQPAE NYKNTQPIMN TNGSYFVYSK  420
LNVQKSNWEA GNTFTCSVLH EGLHNHHTEK SLSHSPGK                          458

SEQ ID NO: 4            moltype = AA  length = 464
FEATURE                 Location/Qualifiers
source                  1..464
                        mol_type = protein
                        organism = synthetic construct
SEQUENCE: 4
MRAWIFFLLC LAGRALAEVR LLQSGGGLVQ PGGSLKLSCA ASGIDFSRYW MSWVRRAPGQ  60
GLEWIGEINP DSSTINYAPS LKDKFIISRD NAKKTLYLQM SKVRSEDKVF YYCAIYYDYA  120
```

```
MDFWGQGTSV TVSSASTKGP SVYPLAPVCG DTTGSSVTLG CLVKGYFPEP VTLTWNSGSL  180
SSGVHTFPAV LQSDLYTLSS SVTVTSSTWP SQSITCNVAH PASSTKVDKK IEPRGPTIKP  240
CPPCKCPAPN LLGGPSVFIF PPKIKDVLMI SLSPIVTCVV VDVSEDDPDV QISWFVNNVE  300
VHTAQTQTHR EDYNSTLRVV SALPIQHQDW MSGKEFKCKV NNKDLPAPIE RTISKPKGSV  360
RAPQVYVLPP PEEEMTKKQV TLTCMVTDFM PEDIYVEWTN NGKTELNYKN TEPVLDSDGS  420
YFMYSKLRVE KKNWVERNSY SCSVVHEGLH NHHTTKSFSR TPGK                  464

SEQ ID NO: 5            moltype = AA  length = 235
FEATURE                 Location/Qualifiers
source                  1..235
                        mol_type = protein
                        organism = synthetic construct
SEQUENCE: 5
MRAWIFFLLC LAGRALADIV LTQSPASLAV SLGQRATISC RASESVDNYG ISFMNWFQQK  60
PGQPPKLLIY AASNQGSGVP ARFSGSGSGT DFSLNIHPME EDDTAMYFCQ QNKEVPYTFG  120
GGTKVEIKRT DAAPTVSIFP PSSEQLTSGG ASVVCFLNNF YPKDINVKWK IDGSERQNGV  180
LNSWTDQDSK DSTYSMSSTL TLTKDEYERH NSYTCEATHK TSTSPIVKSF NRNEC       235

SEQ ID NO: 6            moltype = DNA  length = 351
FEATURE                 Location/Qualifiers
source                  1..351
                        mol_type = other DNA
                        organism = synthetic construct
SEQUENCE: 6
gaagtcagat tgctccagag tggaggtggt ctggttcagc ctggagggtc attgaaactt  60
tcttgcgctg catcaggcat tgatttctct cgctactgga tgtcatgggt tagacgcgct  120
cccggtcaag gtctggagtg gatcggcgag ataaacccgg attcttctac cattaattac  180
gcacctagcc tcaaggacaa atttattatt agccgggata atgcaaaaaa gacattgtac  240
ctccagatgt ccaaggtcag aagcgaggac aaagtcttct actattgtgc aatttattac  300
gattacgcta tggacttctg gggacagggt acatctgtta ctgtatcctc a           351

SEQ ID NO: 7            moltype = DNA  length = 339
FEATURE                 Location/Qualifiers
source                  1..339
                        mol_type = other DNA
                        organism = synthetic construct
SEQUENCE: 7
gacatcgttc ttacgcaatc tccagcctct ttggctgtat ctctcggcca acgagcgacc  60
atttcatgtc gcgcaagcga atcagtagac aattacggta tctcattcat gaactggttc  120
cagcaaaagc caggccaacc accgaagctg ttgatctacg cagcatcaaa tcagggcagt  180
ggcgtaccag cacggttttc aggtagtgga agtgggacag atttttcact caacattcat  240
cctatggaag aagatgatac ggccatgtac ttttgccagc aaaacaagga ggttccctat  300
acgtttggcg gtggcacgaa agtagaaata aagcgtacg                         339

SEQ ID NO: 8            moltype = DNA  length = 1380
FEATURE                 Location/Qualifiers
source                  1..1380
                        mol_type = other DNA
                        organism = synthetic construct
SEQUENCE: 8
atgagggctt ggatcttctt tctgctctgc ctggccgggc gcgccttggc cgaagtcaga  60
ttgctccaga gtggaggtgg tctggttcag cctggagggt cattgaaact ttcttgcgct  120
gcatcaggca ttgatttctc tcgctactgg atgtcatggg ttagacgcgc tcccggtcaa  180
ggtctggagt ggatcggcga gataaacccg gattcttcta ccattaatta cgcacctagc  240
ctcaaggaca aatttattat tagccgggat aatgcaaaaa agacattgta cctccagatg  300
tccaaggtca gaagcgagga caaagtcttc tactattgtg caatttatta cgattacgct  360
atggacttct ggggacaggg tacatctgtt actgtatcct cagccaaaac gacaccccca  420
tctgtctatc cactggcccc tggatctgct gcccaaacta actctatggt gaccctggga  480
tgcctggtca agggctattt ccctgagcca gtgacagtga cctggaactc tggctccctg  540
tccagcggtg tgcacacctt cccagctgtc ctgcagtctg acctctacac tctgagcagc  600
tcagtgactg tcccctccag cacctggccc agcgagaccg tcacctgcaa cgttgcccac  660
ccggccagca gcaccaaggt ggacaagaaa attgtgccca gggattgtgg ttgtaagcct  720
tgcatatgta cagtcccaga agtatcatct gtcttcatct tccccccaaa gcccaaggat  780
gtgctcacca ttactctgac tcctaaggtc acgtgtgttg tggtagacat cagcaaggat  840
gatcccgagg tccagttcag ctggtttgta gatgatgtgg aggtgcacac agctcagacg  900
caaccccgcg aagagcagtt caacagcact ttccgctcag tcagtgaact tcccatcatg  960
caccaggact ggcccaatgg caaggagttc aaatgcaggg tcaacagcgc agctttccct  1020
gcccccatcg agaaaaccat ctccaaaacc aaaggcagac cgaaggctcc acaggtgtac  1080
accattccac ctcccaagga gcagatggcc aaggataaag tcagtctgac ctgcatgata  1140
acagacttct tccctgaaga cattactgtg gagtggcagt ggaatgggca gccagcggag  1200
aactacaaga acactcagcc cattatgaac acgaatggct cttacttcgt ctacagcaag  1260
ctcaatgtcc agaagagcaa ctgggaggca ggaaatactt tcacctgctc tgtgttacat  1320
gagggcctgc ataaccacca tactgagaag agcctctccc actctcctgg taaatgataa  1380

SEQ ID NO: 9            moltype = DNA  length = 1398
FEATURE                 Location/Qualifiers
source                  1..1398
                        mol_type = other DNA
                        organism = synthetic construct
```

```
SEQUENCE: 9
atgagggctt ggatcttctt tctgctctgc ctggccgggc gcgccttggc cgaagtcaga  60
ttgctccaga gtggaggtgg tctggttcag cctggagggt cattgaaact ttcttgcgct  120
gcatcaggca ttgatttctc tcgctactgg atgtcatggg ttagacgcgc tcccggtcaa  180
ggtctggagt ggatcggcga gataaacccg gattcttcta ccattaatta cgcacctagc  240
ctcaaggaca aatttattat tagccgggat aatgcaaaaa agacattgta cctccagatg  300
tccaaggtca gaagcgagga caaagtcttc tactattgtg caatttatta cgattacgct  360
atggacttct ggggacaggg tacatctgtt actgtatcct cagcctccac caagggccca  420
tcggtctatc cactggcccc tgtgtgtgga gatacaactg gctcctcggt gactctagga  480
tgcctggtca agggttattt ccctgagcca gtgaccttga cctggaactc tggatccctg  540
tccagtggtg tgcacacctt cccagctgtc ctgcagtctg acctctacac cctcagcagc  600
tcagtgactg taacctcgag cacctggccc agccagtcca tcacctgcaa tgtggcccac  660
ccggcaagca gcaccaaggt ggacaagaaa attgagccca gaggccccac aatcaagccc  720
tgtcctccat gcaaatgccc agcacctaac ctcttgggtg gaccatccgt cttcatcttc  780
cctccaaaga tcaaggatgt actcatgatc tccctgagcc ccatagtcac atgtgtggtg  840
gtggatgtga gcgaggatga cccagatgtc cagatcagct ggtttgtgaa caacgtggaa  900
gtacacacag ctcagacaca aacccataga gaggattaca acagtactct ccgggtggtc  960
agtgccctcc ccatccagca ccaggactgg atgagtggca aggagttcaa atgcaaggtc  1020
aacaacaaag acctcccagc gcccatcgag agaaccatct caaaacccaa agggtcagta  1080
agagctccac aggtatatgt cttgcctcca ccagaagaag agatgactaa gaaacaggtc  1140
actctgacct gcatggtcac agacttcatg cctgaagaca tttacgtgga gtggaccaac  1200
aacgggaaaa cagagctaaa ctacaagaac actgaaccag tcctggactc tgatggttct  1260
tacttcatgt acagcaagct gagagtggaa aagaagaact gggtggaaag aaatagctac  1320
tcctgttcag tggtccacga gggtctgcac aatcaccaca cgactaagag cttctcccgg  1380
actccgggta aatgataa                                                1398

SEQ ID NO: 10          moltype = DNA  length = 711
FEATURE                Location/Qualifiers
source                 1..711
                       mol_type = other DNA
                       organism = synthetic construct
SEQUENCE: 10
atgagggctt ggatcttctt tctgctctgc ctggccgggc gcgcccttgc cgacatcgtt  60
cttacgcaat ctccagcctc tttggctgta tctctcggcc aacgagcgac catttcatgt  120
cgcgcaagcg aatcagtaga caattacggt atctcattca tgaactggtt ccagcaaaag  180
ccaggccaac caccgaagct gttgatctac gcagcatcaa atcagggcag tggcgtacca  240
gcacggtttt caggtagtgg aagtgggaca gatttttcac tcaacattca tcctatggaa  300
gaagatgata cggccatgta cttttgccag caaaacaagg aggttcccta tacgtttggc  360
ggtggcacga aagtagaaat aaagcgtacg gatgctgcac caactgtatc catcttccca  420
ccatccagtg agcagttaac atctggaggt gcctcagtcg tgtgcttctt gaacaacttc  480
taccccaaag acatcaatgt caagtggaag attgatggca gtgaacgaca aaatggcgtc  540
ctgaacagtt ggactgatca ggacagcaaa gacagcacct acagcatgag cagcaccctc  600
acgttgacca aggacgagta tgaacgacat aacagctata cctgtgaggc cactcacaag  660
acatcaactt cacccattgt caagagcttc aacaggaatg agtgttgata a           711

SEQ ID NO: 11          moltype = AA  length = 8
FEATURE                Location/Qualifiers
source                 1..8
                       mol_type = protein
                       organism = synthetic construct
SEQUENCE: 11
GIDFSRYW                                                           8

SEQ ID NO: 12          moltype = AA  length = 8
FEATURE                Location/Qualifiers
source                 1..8
                       mol_type = protein
                       organism = synthetic construct
SEQUENCE: 12
INPDSSTI                                                           8

SEQ ID NO: 13          moltype = AA  length = 10
FEATURE                Location/Qualifiers
source                 1..10
                       mol_type = protein
                       organism = synthetic construct
SEQUENCE: 13
AIYYDYAMDF                                                         10

SEQ ID NO: 14          moltype = AA  length = 10
FEATURE                Location/Qualifiers
source                 1..10
                       mol_type = protein
                       organism = synthetic construct
SEQUENCE: 14
ESVDNYGISF                                                         10

SEQ ID NO: 15          moltype =   length =
SEQUENCE: 15
```

-continued

```
000

SEQ ID NO: 16           moltype = AA  length = 9
FEATURE                 Location/Qualifiers
source                  1..9
                        mol_type = protein
                        organism = synthetic construct
SEQUENCE: 16
QQNKEVPYT                                                           9

SEQ ID NO: 17           moltype = DNA  length = 24
FEATURE                 Location/Qualifiers
source                  1..24
                        mol_type = other DNA
                        organism = synthetic construct
SEQUENCE: 17
ggcattgatt tctctcgcta ctgg                                          24

SEQ ID NO: 18           moltype = DNA  length = 24
FEATURE                 Location/Qualifiers
source                  1..24
                        mol_type = other DNA
                        organism = synthetic construct
SEQUENCE: 18
ataaacccgg attcttctac catt                                          24

SEQ ID NO: 19           moltype = DNA  length = 30
FEATURE                 Location/Qualifiers
source                  1..30
                        mol_type = other DNA
                        organism = synthetic construct
SEQUENCE: 19
gcaatttatt acgattacgc tatggacttc                                    30

SEQ ID NO: 20           moltype = DNA  length = 30
FEATURE                 Location/Qualifiers
source                  1..30
                        mol_type = other DNA
                        organism = synthetic construct
SEQUENCE: 20
gaatcagtag acaattacgg tatctcattc                                    30

SEQ ID NO: 21           moltype =   length =
SEQUENCE: 21
000

SEQ ID NO: 22           moltype = DNA  length = 27
FEATURE                 Location/Qualifiers
source                  1..27
                        mol_type = other DNA
                        organism = synthetic construct
SEQUENCE: 22
cagcaaaaca aggaggttcc ctatacg                                       27
```